(12) United States Patent
Dai et al.

(10) Patent No.: US 12,109,166 B2
(45) Date of Patent: Oct. 8, 2024

(54) COOLING AND HEATING MASSAGER

(71) Applicant: ThreeSixty Sourcing Limited, Hong Kong (CN)

(72) Inventors: Quanqin Dai, Walnut, CA (US); Yong Yu, Diamond Bar, CA (US); Guorong Xu, Yuyao (CN)

(73) Assignee: MerchSource, LLC, Irvine, CA (US)

(*) Notice: Subject to any disclaimer, the term of this patent is extended or adjusted under 35 U.S.C. 154(b) by 0 days.

(21) Appl. No.: 17/982,324

(22) Filed: Nov. 7, 2022

(65) Prior Publication Data

US 2023/0090085 A1 Mar. 23, 2023

Related U.S. Application Data

(63) Continuation of application No. 16/675,718, filed on Nov. 6, 2019, now Pat. No. 11,877,976.

(51) Int. Cl.
*A61H 23/02* (2006.01)
*A61F 7/00* (2006.01)
*A61H 23/00* (2006.01)

(52) U.S. Cl.
CPC ........... *A61H 23/0254* (2013.01); *A61F 7/00* (2013.01); *A61H 23/006* (2013.01);
(Continued)

(58) Field of Classification Search
CPC .............. A61H 23/006; A61H 23/0263; A61H 2201/0207; A61H 2201/0214;
(Continued)

(56) References Cited

U.S. PATENT DOCUMENTS 5,097,828 A * 3/1992 Deutsch .................. A61F 7/007
604/113
6,241,027 B1 6/2001 Beck et al.
(Continued)

FOREIGN PATENT DOCUMENTS

CN 201150633 11/2008
CN 201267597 7/2009
(Continued)

OTHER PUBLICATIONS

Machine translation of KR-10-20170098577 (Year: 2017).*
(Continued)

*Primary Examiner* — Timothy A Stanis
(74) *Attorney, Agent, or Firm* — Avyno Law P.C.

(57) ABSTRACT

A system to provide physical therapy in the form of heating, cooling and/or percussion, comprising: a device that contains a battery, a motor, and a switch to turn the device on or off or put the device in heating mode or put the device in cooling mode or put the device in percussion mode; wherein the device contains a motor and a pushing rod that supply the movement that results in percussion of a removable heating/cooling attachment and a removable percussion attachment; wherein the front of the device connects to the removable heating/cooling attachment that contains an electronic component to control heating or cooling and a cooling fan; wherein the removable heating/cooling attachment can be used for heating or cooling; wherein a housing shell for the heating/cooling attachment is made of plastic, foam, or metal, or any combination of plastic, foam and metal; wherein the front part of the heating/cooling attachment is made of metal that has the capability to be in contact with human skin in order to provide either heating or cooling at fixed or adjusted degrees that are optimal for physical therapy and/or blood circulation; wherein the removable heating/cooling attachment can be replaced by the remov- (Continued)

able percussion attachment that is used for percussion; wherein the removable percussion attachment can be placed on the skin of a user in order to provide percussion at fixed or adjusted speeds that are optimal for physical therapy.

24 Claims, 23 Drawing Sheets

(52) U.S. Cl.
CPC .. *A61H 23/0263* (2013.01); *A61F 2007/0064* (2013.01); *A61H 2201/0207* (2013.01); *A61H 2201/0214* (2013.01); *A61H 2201/025* (2013.01); *A61H 2201/149* (2013.01); *A61H 2201/5025* (2013.01); *A61H 2209/00* (2013.01)

(58) Field of Classification Search
CPC ........ A61H 2201/025; A61H 2201/149; A61H 2201/5025; A61F 7/00
See application file for complete search history.

(56) References Cited

U.S. PATENT DOCUMENTS

| | | | |
|---|---|---|---|
| 6,432,072 B1 | 8/2002 | Harris et al. | |
| 6,682,496 B1 | 1/2004 | Pivaroff | |
| 7,273,159 B2 | 9/2007 | Brotto | |
| 7,384,405 B2 | 6/2008 | Rhoades | |
| 8,713,739 B1 | 5/2014 | Alas et al. | |
| 9,089,470 B2 | 7/2015 | Lev et al. | |
| 10,314,762 B1 | 6/2019 | Marton et al. | |
| 2001/0007952 A1 | 7/2001 | Shimizu | |
| 2002/0177795 A1 | 11/2002 | Frye | |
| 2003/0229300 A1 | 12/2003 | Winkley | |
| 2005/0020947 A1 | 1/2005 | Dehli | |
| 2005/0203445 A1 | 9/2005 | Tsai | |
| 2005/0209537 A1 | 9/2005 | Gleason et al. | |
| 2005/0209539 A1 | 9/2005 | Lev et al. | |
| 2006/0058714 A1 | 3/2006 | Rhoades | |
| 2008/0014011 A1 | 1/2008 | Rossen | |
| 2008/0119767 A1 | 5/2008 | Berry et al. | |
| 2008/0300529 A1 | 12/2008 | Reinstein | |
| 2010/0274162 A1* | 10/2010 | Evans | A61H 15/0092 601/46 |
| 2013/0046212 A1 | 2/2013 | Nichols | |
| 2014/0276255 A1 | 9/2014 | McGushion | |
| 2014/0378555 A1 | 12/2014 | Hung et al. | |
| 2015/0005682 A1 | 1/2015 | Danby et al. | |
| 2015/0121900 A1 | 5/2015 | Yamazaki | |
| 2015/0182290 A1 | 7/2015 | Grez | |
| 2015/0297393 A1 | 10/2015 | McGushion | |
| 2015/0305969 A1* | 10/2015 | Giraud | A61H 7/005 601/84 |
| 2016/0089537 A1 | 3/2016 | Yamazaki | |
| 2016/0151238 A1 | 6/2016 | Crunick et al. | |
| 2016/0331308 A1 | 11/2016 | Zhou | |
| 2016/0367425 A1 | 12/2016 | Wersland | |
| 2017/0304145 A1* | 10/2017 | Pepe | A61H 23/02 |
| 2018/0185236 A1 | 7/2018 | Levi | |
| 2018/0200141 A1 | 7/2018 | Wersland et al. | |
| 2018/0228691 A1 | 8/2018 | Marton et al. | |
| 2018/0263845 A1 | 9/2018 | Wersland et al. | |
| 2018/0280675 A1* | 10/2018 | Tharp | A61M 5/32 |
| 2019/0015294 A1 | 1/2019 | Nazarian et al. | |
| 2019/0015295 A1 | 1/2019 | Marton et al. | |
| 2019/0060115 A1 | 2/2019 | Novkov et al. | |
| 2019/0136889 A1 | 5/2019 | Wersland et al. | |
| 2019/0159961 A1 | 5/2019 | Chuang | |
| 2019/0175434 A1 | 6/2019 | Zhang | |
| 2020/0155410 A1 | 5/2020 | Smith, Jr. et al. | |
| 2020/0268594 A1 | 8/2020 | Pepe | |
| 2020/0289161 A1 | 9/2020 | Scooros | |
| 2021/0077340 A1* | 3/2021 | Pepe | A61H 19/30 |
| 2022/0117073 A1* | 4/2022 | Wandke | A61N 1/44 |
| 2022/0233397 A1* | 7/2022 | Huang | A61H 23/0254 |

FOREIGN PATENT DOCUMENTS

| | | | |
|---|---|---|---|
| CN | 110025466 A | 7/2019 | |
| JP | 6096570 B2 | 3/2017 | |
| KR | 100539364 B1 | 1/2006 | |
| KR | 100746214 B1 | 8/2007 | |
| KR | 101578689 B1 | 12/2015 | |
| KR | 10-2017-0098577 * | 8/2017 | ............ A61H 23/02 |
| KR | 2017098577 | 8/2017 | |
| KR | 2020170003668 U | 10/2017 | |
| KR | 101810511 B1 | 12/2017 | |
| TW | M572227 U | 1/2019 | |
| WO | 2014147855 A1 | 9/2014 | |

OTHER PUBLICATIONS

Amazon "HoMedics Percussion Pro Handheld Massager with Heat" (2018). (Year:2018).

Memmert, "Advanced Peltier Technology", Jul. 5, 2017. (Year: 2017).

* cited by examiner

COOLING AND HEATING MASSAGER

CROSS-REFERENCE TO RELATED APPLICATIONS

The application claims priority to U.S. patent application Ser. No. 16/675,718, titled PHYSICAL THERAPY DEVICE WITH PERCUSSION, COOLING, AND HEATING, filed on Nov. 6, 2019, which application is incorporated herein in its entirety.

FIELD OF INVENTION

The invention relates to a massage node having a heating and cooling features, and in particular a massage node having heating and cooling features for use with a percussion massager.

BACKGROUND

There are several massage products in which a motor is part of a handheld device in the shape of a gun. There are also several products that provide heating or cooling feelings utilizing electric power. Some of these devices specifically target the health of human beings, such as a deep muscle stimulation device. There are also electric massage devices, some of which limit their speeds to certain frequencies.

There are also homemade jigsaw devices that use percussion; these involve off the shelf components that are not particularly suited to the purpose of massaging. These devices are also not measured to exact specifications. These homemade devices can also involve components that are not meant to be anywhere near human skin, and so are particularly dangerous. Some of these devices utilize golf balls or other spherical objects that likely will not be comfortable on human skin, and of course was never intended to touch human skin with force.

The background description includes information that may be useful in understanding the present invention. It is not an admission that any of the information provided herein is prior art or relevant to the presently claimed invention, or that any publication specifically or implicitly referenced is prior art.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. The following description includes information that may be useful in understanding the present invention. It is not an admission that any of the information provided herein is prior art or relevant to the presently claimed invention, or that any publication specifically or implicitly referenced is prior art.

In some embodiments, the numbers expressing quantities of ingredients, properties such as concentration, reaction conditions, and so forth, used to describe and claim certain embodiments of the invention are to be understood as being modified in some instances by the term "about."

Accordingly, in some embodiments, the numerical parameters set forth in the written description and attached claims are approximations that can vary depending upon the desired properties sought to be obtained by a particular embodiment.

In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a", "an" and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "Such as") provided with respect to certain embodiments herein is intended merely to better illuminate the invention and does not pose a limitation on the scope of the invention otherwise claimed.

No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

SUMMARY

The present invention provides the unique combination of either heating or cooling along with percussion. This combination can accelerate the blood circulation and even recovery for people with pain. It is a unique combination because previously only temperate based devices or percussion based devices existed separately, however the present invention combines them, and adds other refinements as well, making it unique. The present invention allows for variations in intensity at optimal speeds for percussion and optimal temperatures for either heating or cooling.

Moreover, the motor innovatively located in the head housing shell of the present invention can shorten the connection of the motor to the pushing rod that constantly moves back and forth to provide percussion. Therefore, the present invention can potentially reduce use of parts and their length between the motor and the pushing rod, and reduce the amount of noise emitted into the workplace or environment from the mechanical connection between the motor and the pushing rod.

DETAILED DESCRIPTION OF THE INVENTION

FIG. 1

Figure 1:
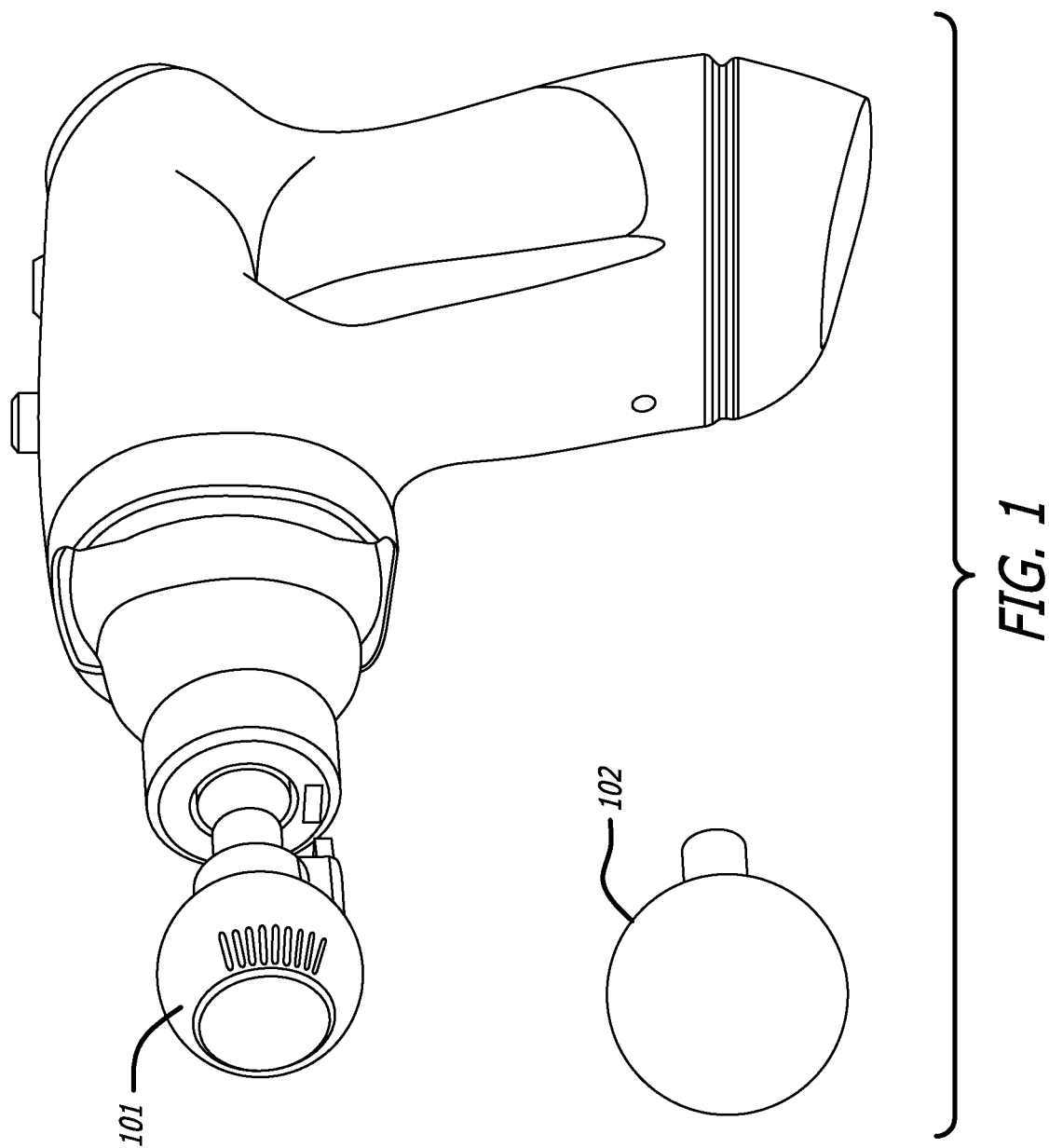
FIG. 1 displays one embodiment of the exterior of the present invention from an oblique side view.

FIG. 1 displays one embodiment of the exterior of the present invention from an oblique side view. The front semi-spherical or spherical part is also shown separated from the rest of the device.

Heating/Cooling attachment 101 is seen separated from the rest of the invention, because it can be removed and reattached, i.e. it is reattachable. The head of the heating/cooling attachment can be of the semi-spherical shape or other shapes.

Percussion attachment 102 is seen as a separate part from the rest of the invention, because it can be removed and reattached, i.e. it is reattachable. The head of the percussion attachment can be of the existing spherical shape or other shapes.

FIG. 2

Figure 2:
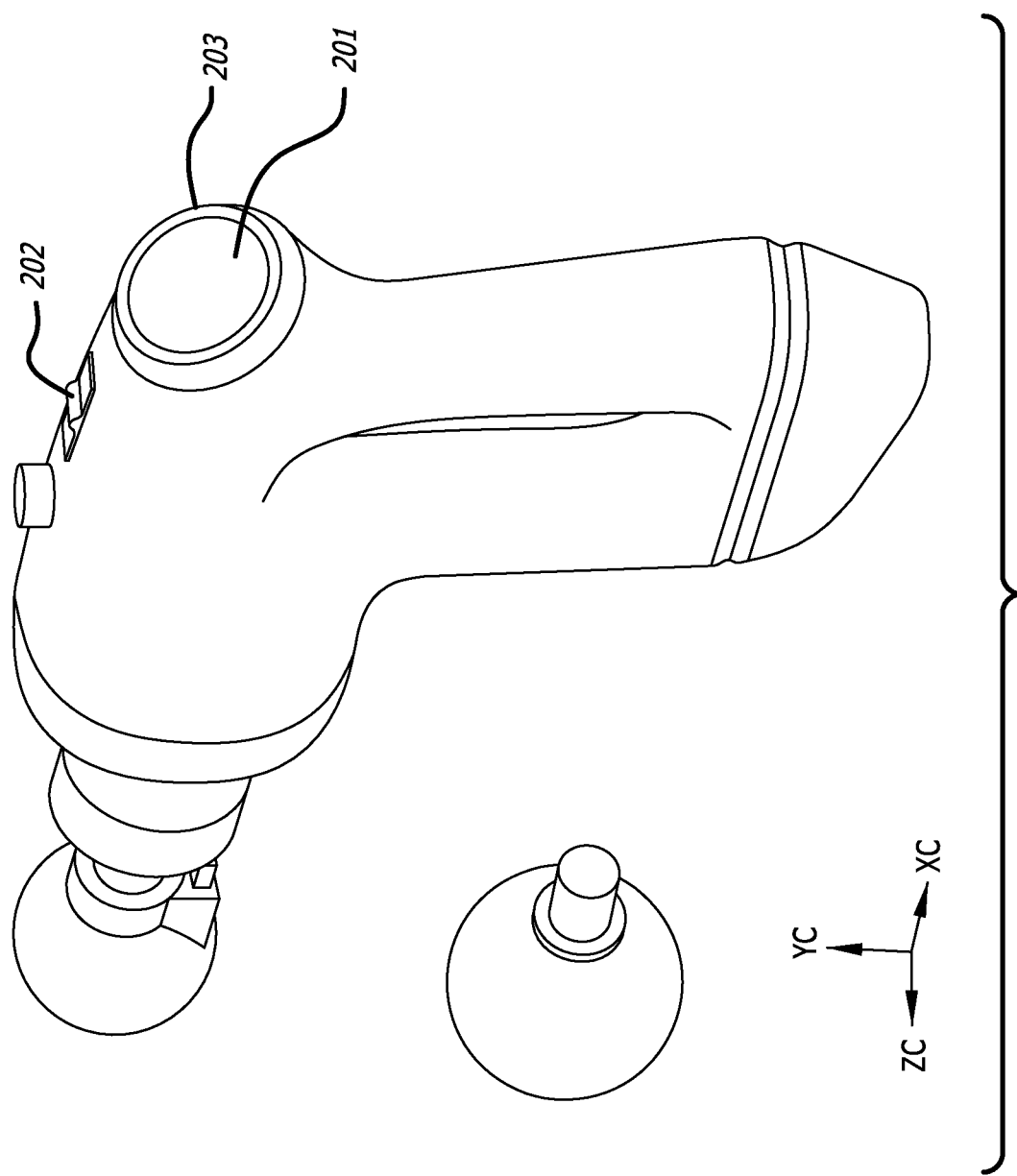
FIG. 2 displays another embodiment of the exterior of the present invention, this time from a rear oblique view as compared to FIG. 1.

FIG. 2 displays another embodiment of the exterior of the present invention, this time from a rear oblique view as compared to FIG. 1.

The rear display 201 is where certain information about the various modes of the invention is displayed. The rear display 201 is in color, and turns on when the invention turns on.

The switch 202 is how the invention is turned on or off, as well as turned from one mode to the next, where the modes consist of percussion, cooling and heating.

The adjustment dial 203 allows for changes in intensity when the invention is in either percussion, cooling or heating mode.

FIG. 3

Figure 3:
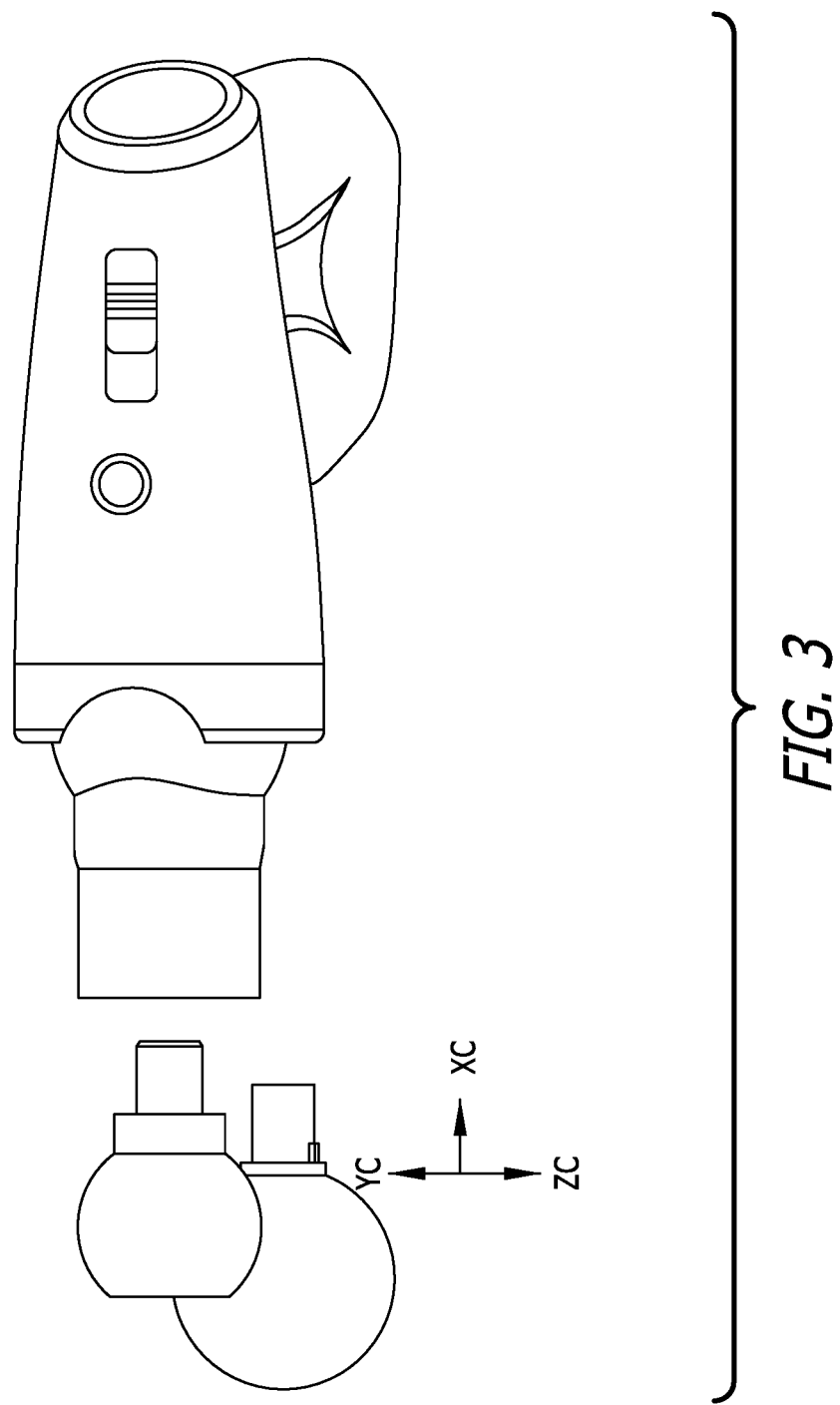
FIG. 3 displays another embodiment of the exterior of the present invention. This is a top view at a slightly oblique angle of the physical therapy device, based on the axis seen in the lower left of the figure.

FIG. 3 displays another embodiment of the exterior of the present invention. This is a top view at a slightly oblique angle of the physical therapy device, based on the axis seen in the lower left of the figure.

FIG. 4

Figure 4:
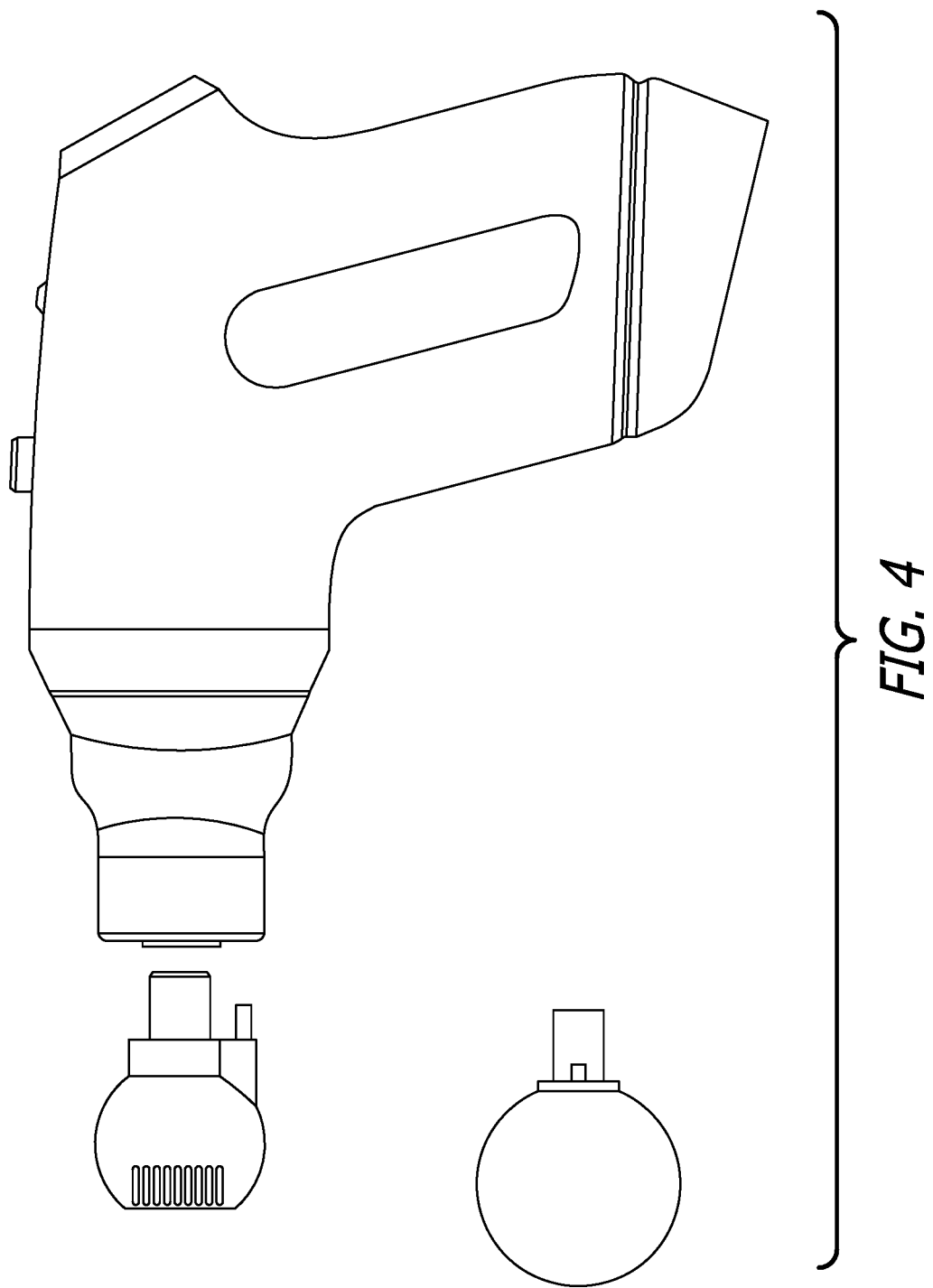
FIG. 4 displays another embodiment of the exterior of the present invention, this time from a side view.

FIG. 4 displays another embodiment of the exterior of the present invention, this time from a side view. The front semi-spherical or spherical part is also shown separated from the rest of the device.

FIG. 5

Figure 5:
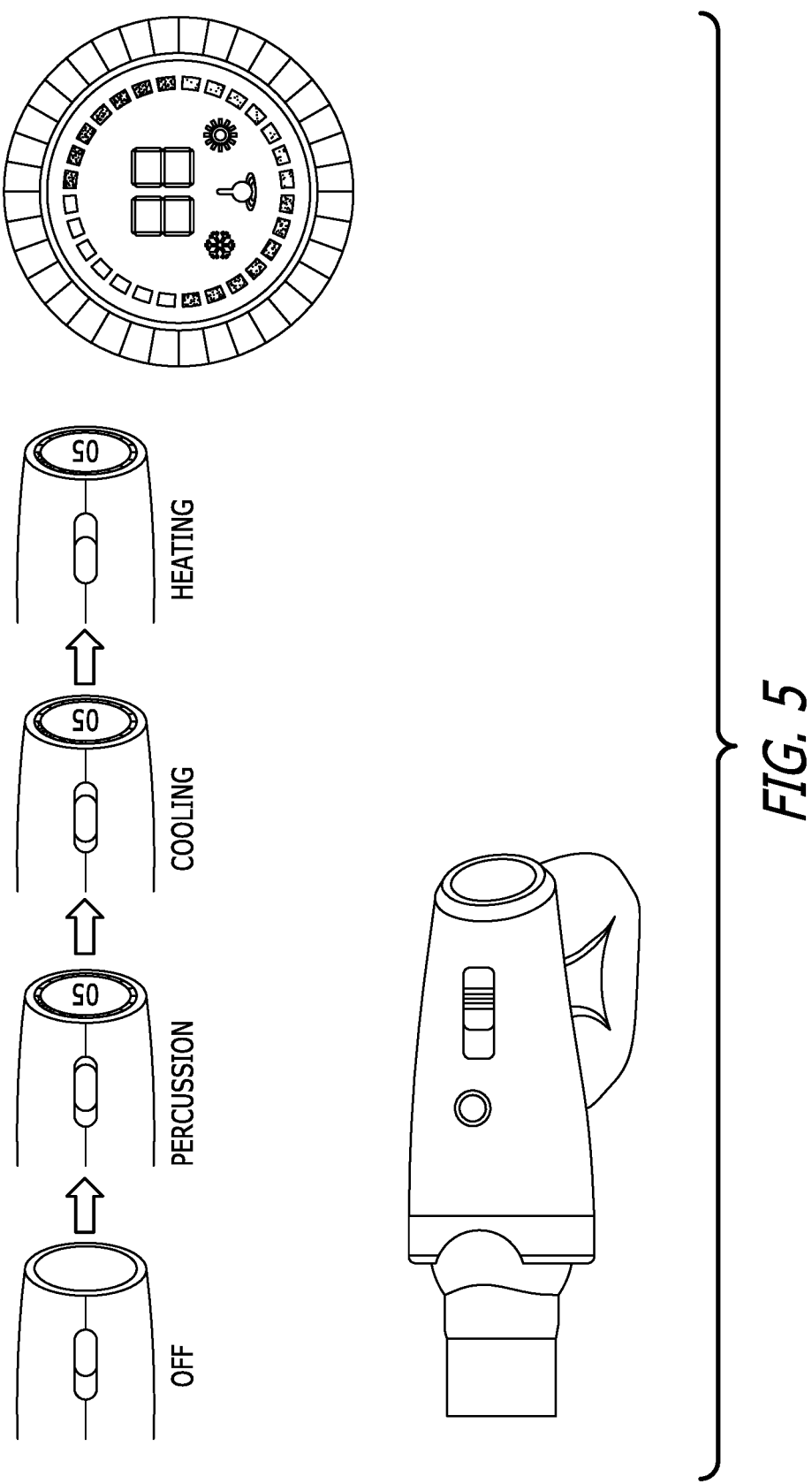
FIG. 5 displays another embodiment of the present invention. Here, the switch of the present invention is examined in the various different states of the switch.

FIG. 5 displays another embodiment of the present invention. Here, the switch of the present invention is examined in the various different states of the switch.

When the switch is entirely to the right, then the invention is off. When the switch moves slightly to the left, the invention enters the percussion mode. When the switch moves slightly more to the left, the invention enters the cooling mode. When the switch moves slightly more to the left, such that the switch is all the way to the left, the invention enters the heating mode.

Upon each different mode, the relevant icon will appear and/or flash on the rear display. So when the percussion mode is selected, the percussion icon will appear and/or flash on the rear display. When the cooling mode is selected, the cooling icon will appear and/or flash on the rear display. When the heating mode is selected, the heating icon will appear and/or flash on the rear display.

The percussion icon is white in color, and is shaped like a circle with a stick pointing out at the top, all filled with white, and where the bottom of the circle is surrounded by a few white lines in a horizontal oval shape.

The cooling icon is a blue snowflake.

The heating icon is a red sun.

FIG. 6

Figure 6:
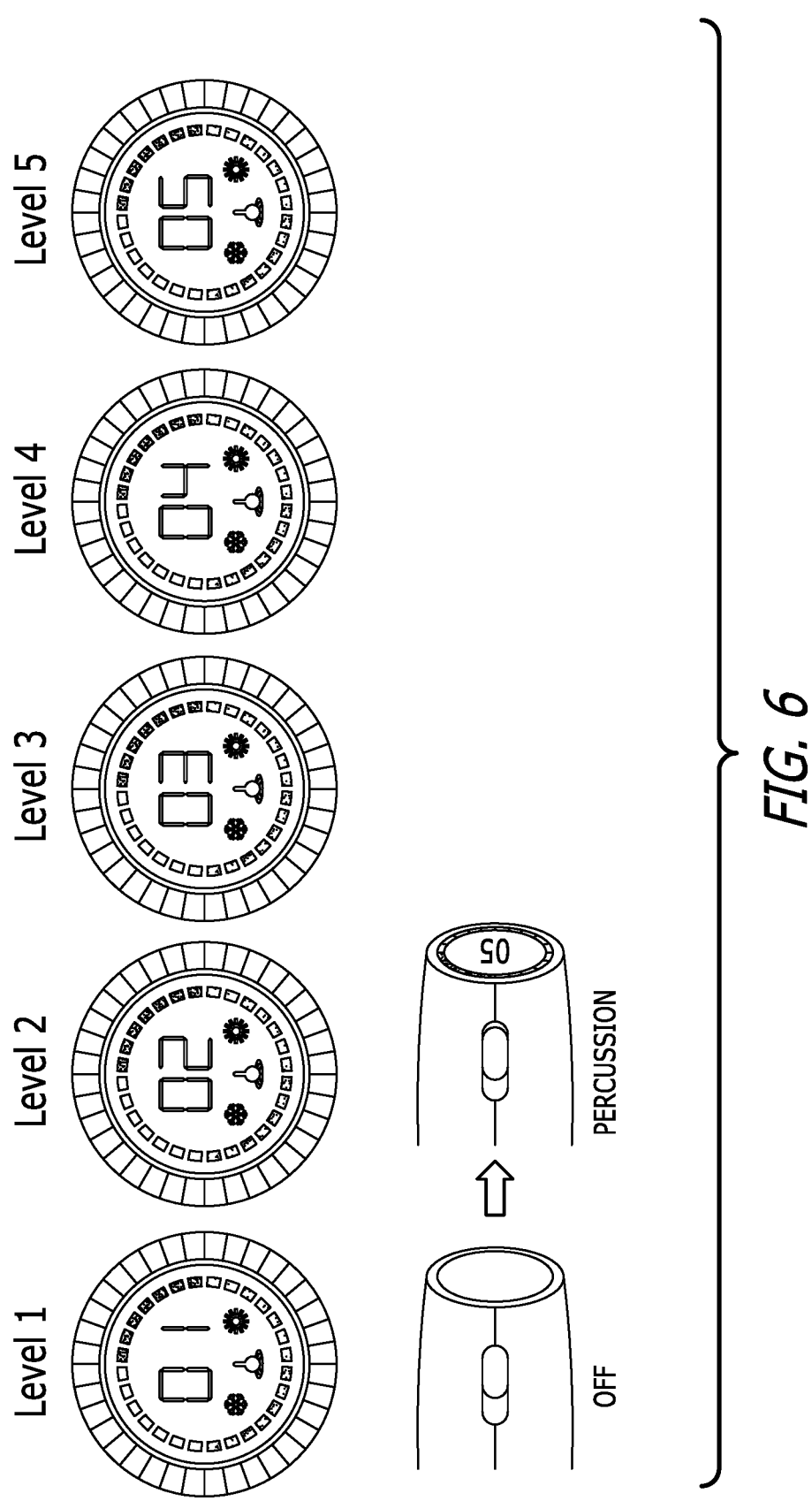
FIG. 6 displays another embodiment of the present invention. After the switch is moved to the percussion mode, the adjustment dial can be used to change intensity levels of percussion. Here, the adjustment dial is shown as it turns through the various intensity levels.

FIG. 6 displays another embodiment of the present invention. After the switch is moved to the percussion mode, the adjustment dial can be used to change intensity levels of percussion. Here, the adjustment dial is shown as it turns through the various intensity levels. It starts at level 1, in which the rear display shows 01. Level 1 corresponds to 900 rpm or 15 Hz. At level 2, the rear display shows 02. Level 2 corresponds to 1200 rpm or 20 Hz. At level 3, the rear display shows 03. Level 3 corresponds to 1800 rpm or 30 Hz. At level 4, the rear display shows 04. Level 4 corresponds to 2400 rpm or 40 Hz. At level 5, the rear display shows 05. Level 5 corresponds to 3300 rpm or 55 Hz. At level 6, the rear display shows 06. Level 6 corresponds to 3900 rpm or 65 Hz. At level 7, the rear display shows 07. Level 7 corresponds to 4500 rpm or 75 Hz. At level 8, the rear display shows 08. Level 8 corresponds to 5100 rpm or 85 Hz. At level 9, the rear display shows 09. Level 9 corresponds to 5700 rpm or 95 Hz. At level 10, the rear display shows 10. Level 10 corresponds to 6000 rpm or 100 Hz.

FIG. 7

Figure 7:
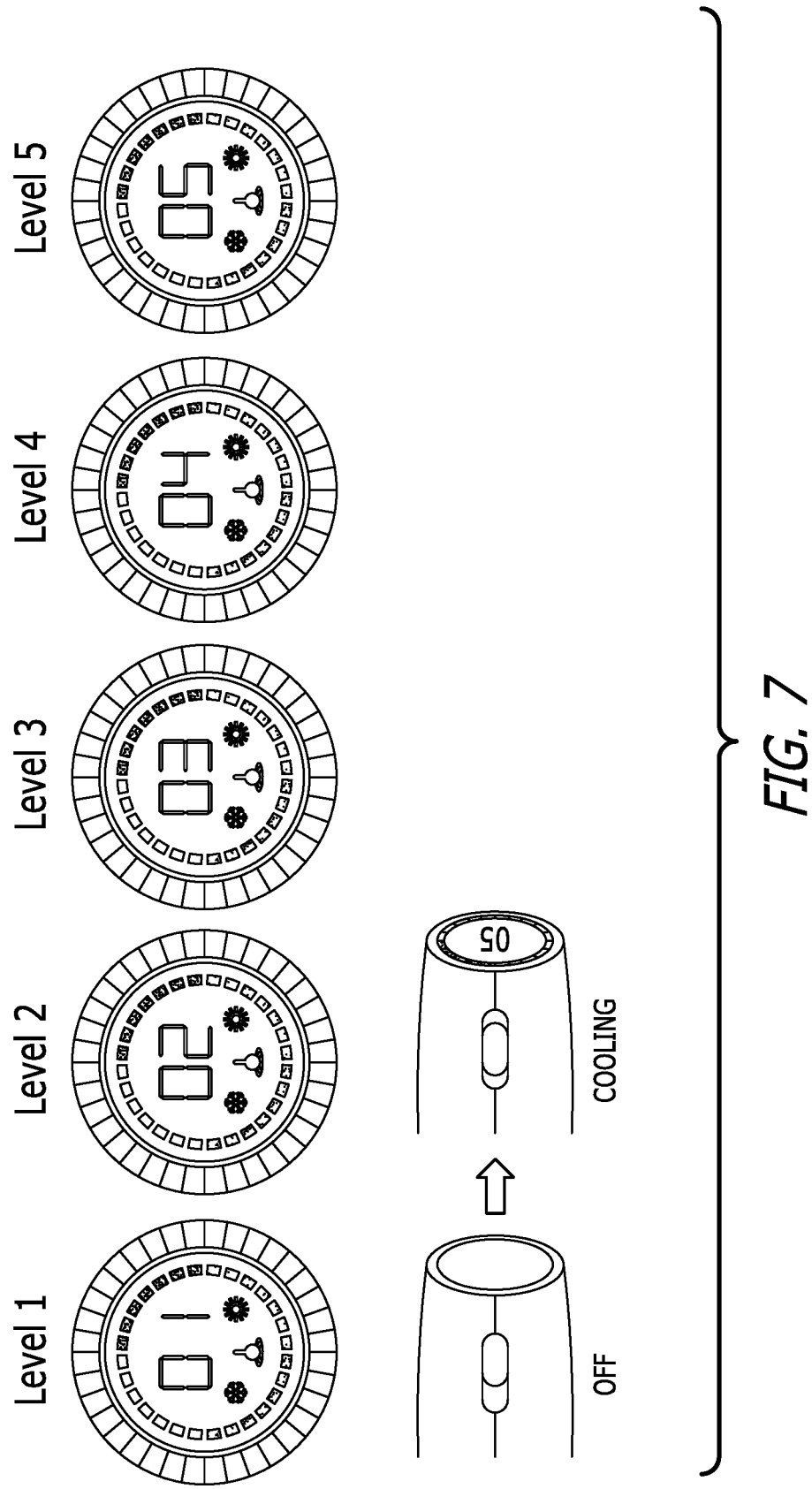
FIG. 7 displays another embodiment of the present invention. After the switch is moved to the cooling mode, the adjustment dial can be used to change intensity levels of cooling. Here, the adjustment dial is shown as it turns through the various intensity levels.

FIG. 7 displays another embodiment of the present invention. After the switch is moved to the cooling mode, the adjustment dial can be used to change intensity levels of cooling. Here, the adjustment dial is shown as it turns through the various intensity levels. It starts at level 1, in which the rear display shows 01. Level 1 corresponds to 6 degrees Celsius. At level 2, the rear display shows 02. Level 2 corresponds to 5 degrees Celsius. At level 3, the rear display shows 03. Level 3 corresponds to 4 degrees Celsius. At level 4, the rear display shows 04. Level 4 corresponds to 3 degrees Celsius. At level 5, the rear display shows 05. Level 5 corresponds to 2 degrees Celsius.

2 degrees Celsius is the lowest temperature that should be directly applied to the skin. Any lower than that, and a user should wear clothing between the invention and the user's skin. At level 6, the rear display shows 06. Level 6 corresponds to 1 degree Celsius. At level 7, the rear display shows 07. Level 7 corresponds to 0 degrees Celsius.

The cooling mode also has a fixed or adjusted percussion rate. In one embodiment of the present invention, the cooling mode's fixed percussion rate is 1200 rpm or 20 Hz.

FIG. 8

Figure 8:
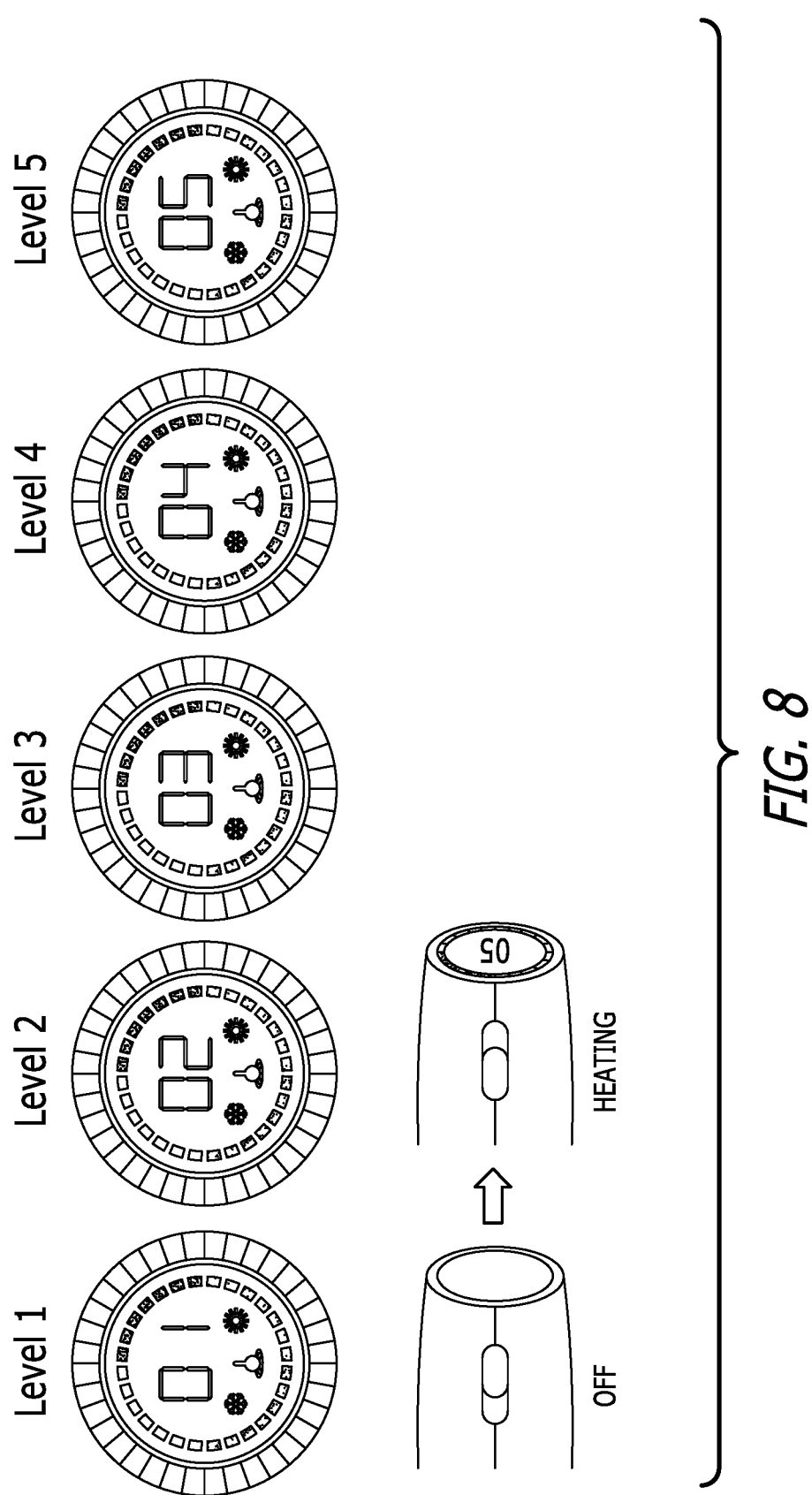
FIG. 8 displays another embodiment of the present invention. After the switch is moved to heating mode, the adjustment dial can be used to change intensity levels of heating. Here, the adjustment dial is shown as it turns through the various intensity levels.

FIG. 8 displays another embodiment of the present invention. After the switch is moved to the heating mode, the adjustment dial can be used to change intensity levels of heating. Here, the adjustment dial is shown as it turns through the various intensity levels. It starts at level 1, in which the rear display shows 01. Level 1 corresponds to 40 degrees Celsius. At level 2, the rear display shows 02. Level 2 corresponds to 41 degrees Celsius. At level 3, the rear display shows 03. Level 3 corresponds to 42 degrees Celsius. At level 4, the rear display shows 04. Level 4 corresponds to 43 degrees Celsius. At level 5, the rear display shows 05. Level 5 corresponds to 44 degrees Celsius.

45 degrees Celsius is the highest temperature that should be directly applied to the skin. Any higher than that, and a user should wear clothing between the invention and the user's skin. Levels 6-36 continue to increase by increments of 1 degree Celsius per level, just like levels 1-5 where the increment was 1 degree Celsius per level. At level 6, the rear display shows 06. Level 6 corresponds to 45 degrees Celsius. At level 7, the rear display shows 07. Level 7 corresponds to 46 degree Celsius. At level 8, the rear display shows 08. Level 8 corresponds to 47 degrees Celsius. At level 9, the rear display shows 09. Level 9 corresponds to 48 degrees Celsius. This continues level by level, degree by degree, until reaching level 36, where the rear display shows 36. Level 36 corresponds to 75 degrees Celsius.

The heating mode also has a fixed or adjusted percussion rate. In one embodiment of the present invention, the heating mode's fixed percussion rate is 1200 rpm or 20 Hz.

FIG. 9

Figure 9:
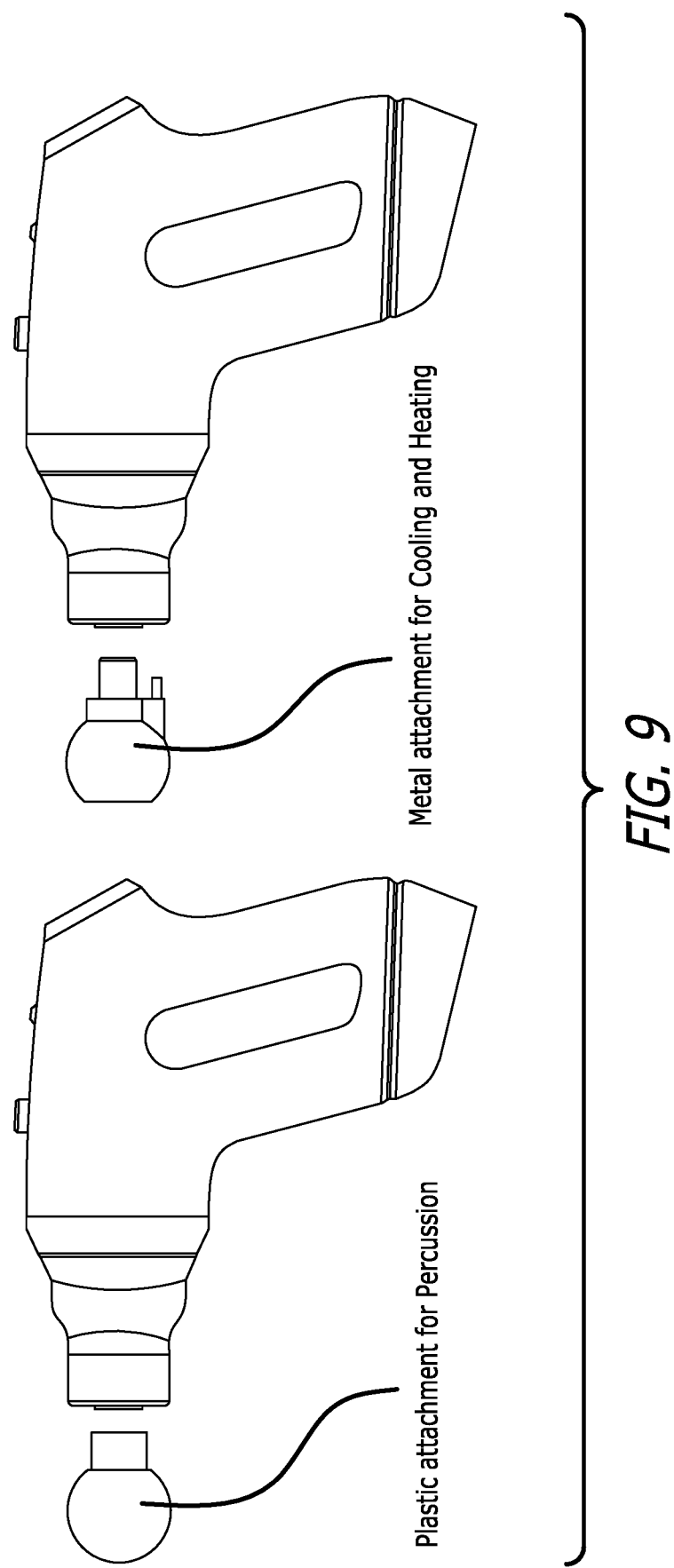
FIG. 9 displays another embodiment of the present invention with different attachments for the front piece.

FIG. 9 displays another embodiment of the present invention with different attachments for the front piece. For percussion mode purposes, there is a percussion attachment as the front piece, which can be made of plastic, foam, metal, or any combination of plastic, foam and metal. For cooling or heating mode purposes, there is a heating/cooling attachment as the front piece. The housing shell for the heating/cooling attachment is made of plastic, foam, or metal, or any combination of plastic, foam and metal. The front part of the heating/cooling attachment is made of metal that has the capability to be in contact with human skin.

FIG. 10

Figure 10:
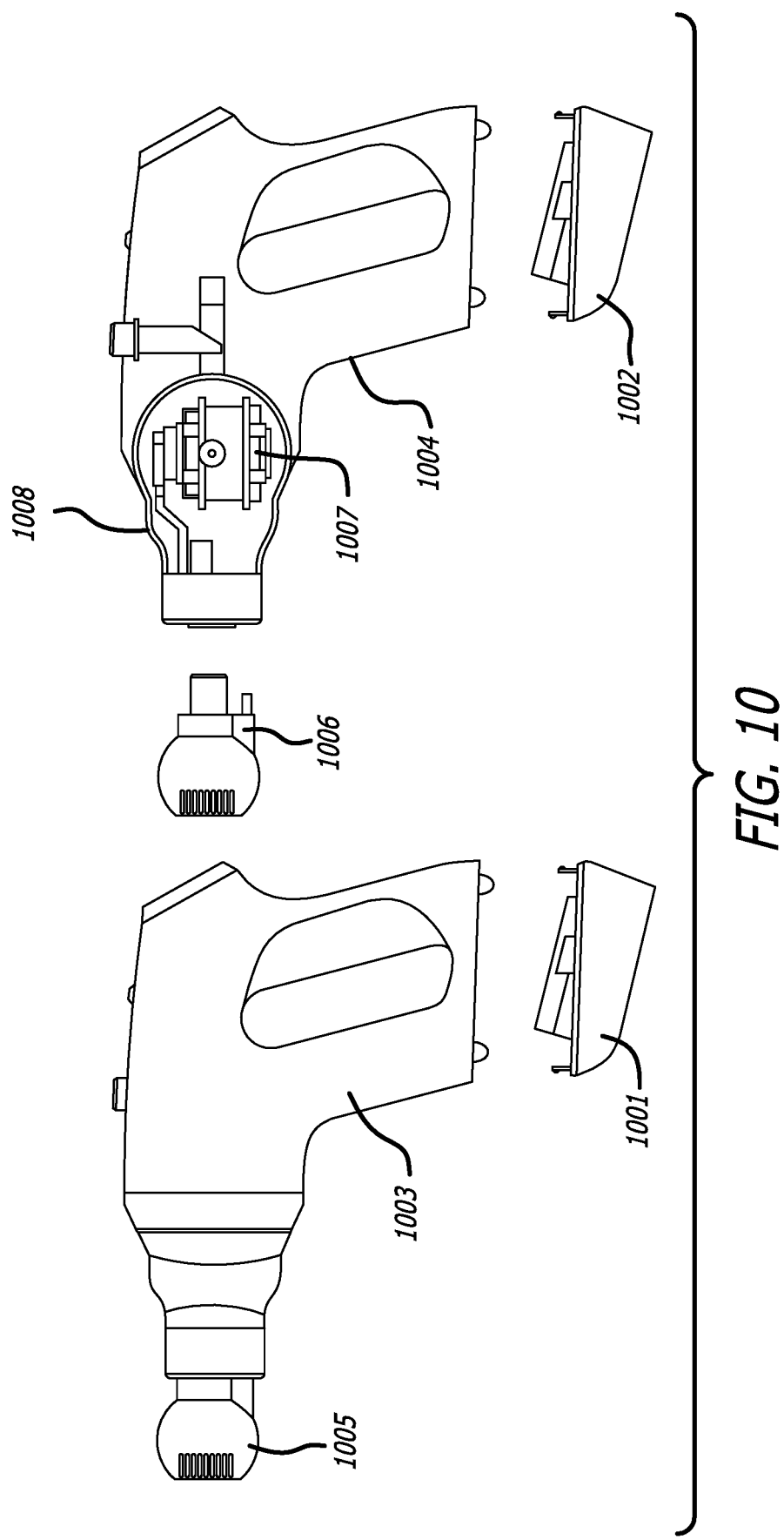
FIG. 10 displays another embodiment of the present invention. The exterior of the removable battery 1001 can be removed from the rest of the invention by detaching it from the bottom.

FIG. 10 displays another embodiment of the present invention. The exterior of the removable battery 1001 can be removed from the rest of the invention by detaching it from the bottom. Removable battery 1002 can also be removed from the rest of the invention by detaching it from the bottom. The front piece 1005 can also be removed from the rest of the invention, and can be seen as removed in the front piece 1006. The main housing shell of the device 1003 is part of an exterior view of the invention. The main housing shell of the device 1004 is part of an internal view of the invention such that various parts and internal devices are visible. The motor 1007 is in the head housing shell 1008, instead of the main housing shell 1004. Therefore, the present invention can shorten the connection between the motor 1007 and the front piece 1006.

FIG. 11

Figure 11:
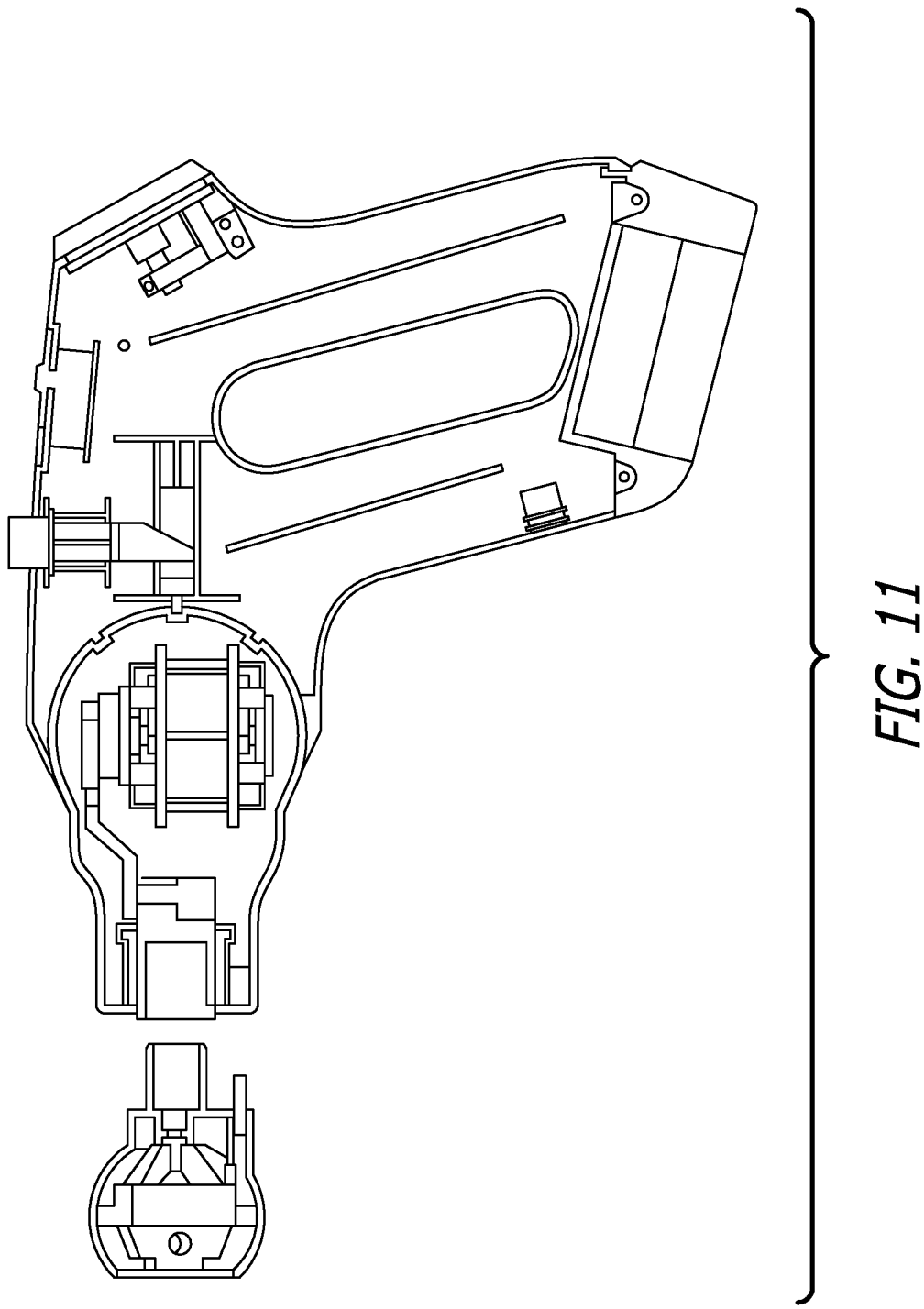
FIG. 11 displays another embodiment of the present invention. This is a sectional view of the physical therapy device at a side angle.

FIG. 11 displays another embodiment of the present invention. This is a sectional view of the physical therapy device at a side angle.

FIG. 12

Figure 12:
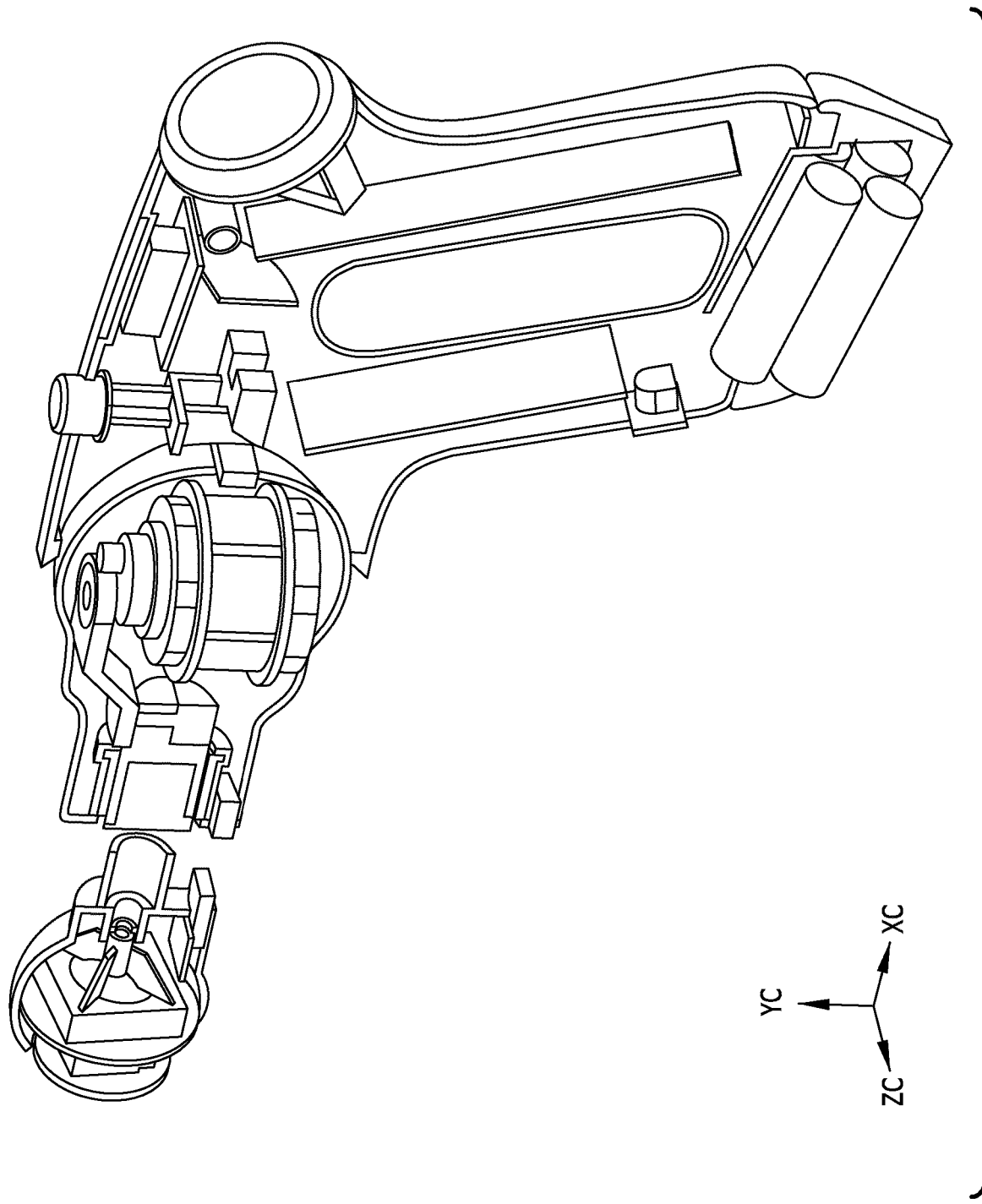
FIG. 12 displays another embodiment of the present invention. This is a sectional view of the physical therapy device at an oblique angle based on the axis seen in the lower left of the figure.

FIG. 12 displays another embodiment of the present invention. This is a sectional view of the physical therapy device at an oblique angle based on the axis seen in the lower left of the figure.

FIG. 13

Figure 13:
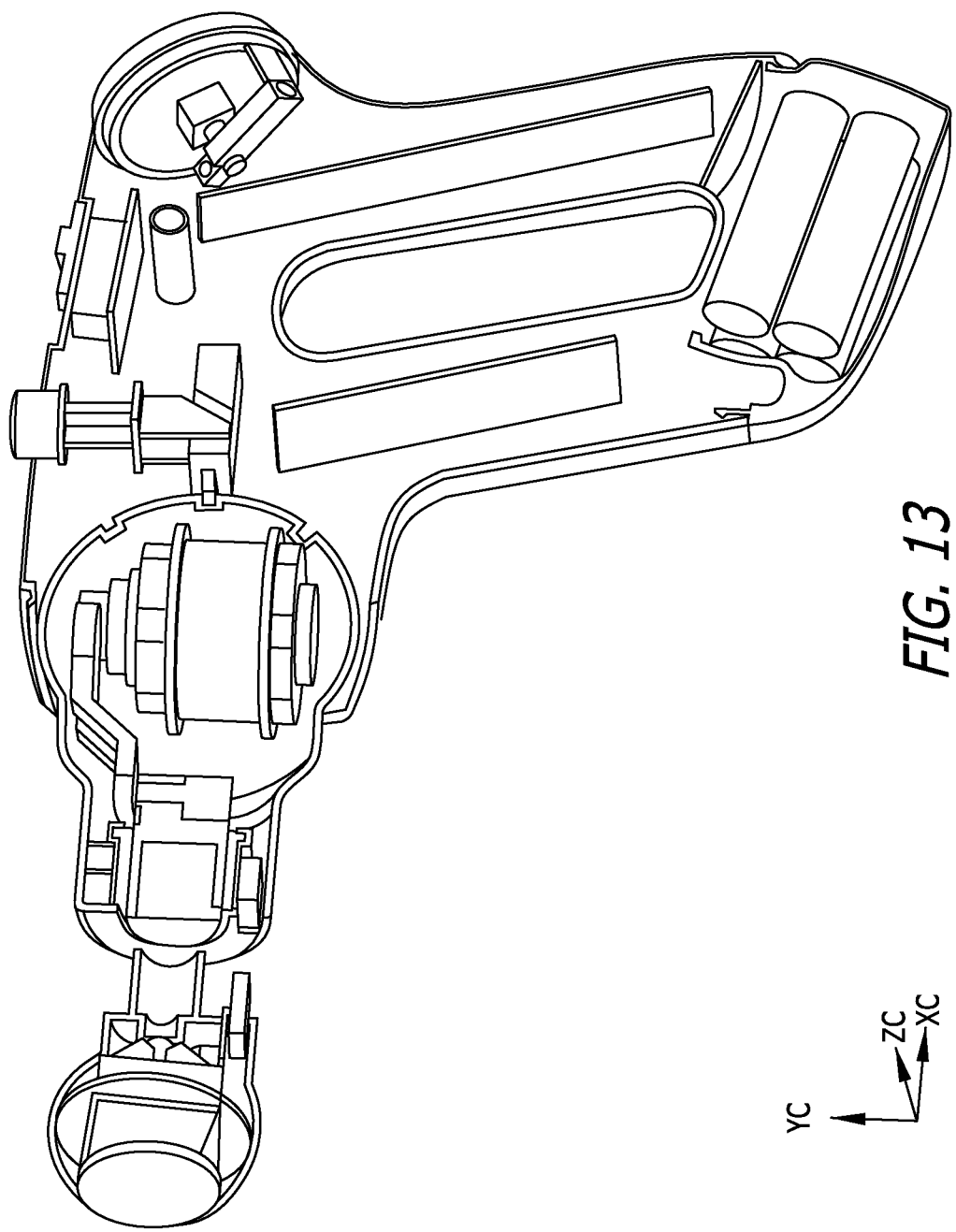
FIG. 13 displays another embodiment of the present invention. This is a sectional view of the physical therapy device at an oblique angle based on the axis seen in the lower left of the figure.

FIG. 13 displays another embodiment of the present invention. This is a sectional view of the physical therapy device at an oblique angle based on the axis seen in the lower left of the figure.

FIG. 14

Figure 14:
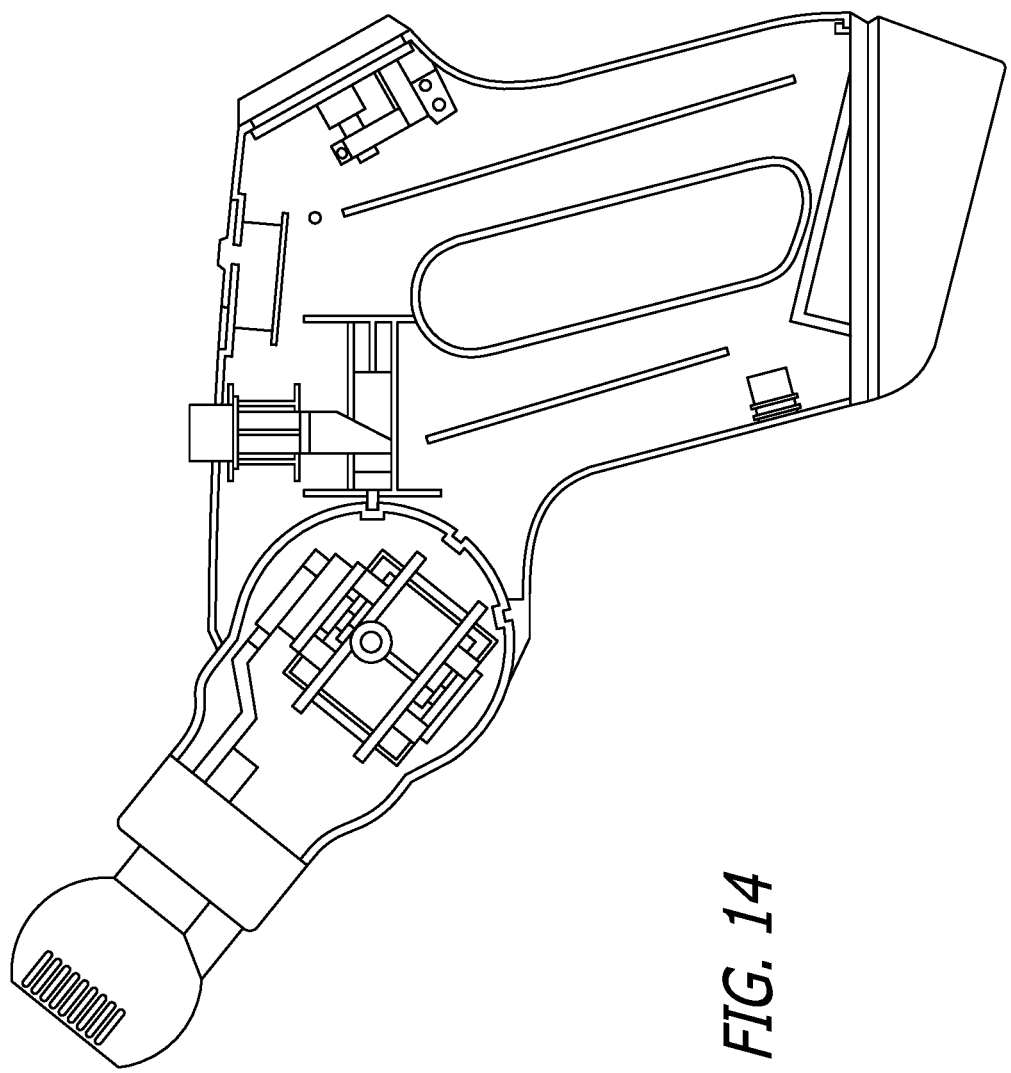
FIG. 14 displays another embodiment of the present invention. This is a sectional view of the physical therapy device in which the front angle of the head housing shell has been adjusted upward.

FIG. 14 displays another embodiment of the present invention. This is a sectional view of the physical therapy device in which the front angle of the head housing shell has been adjusted upward. The motor is in the head housing shell, instead of the main housing shell. Therefore, the whole head housing shell, instead of part of it, can be adjusted upward.

FIG. 15

Figure 15:
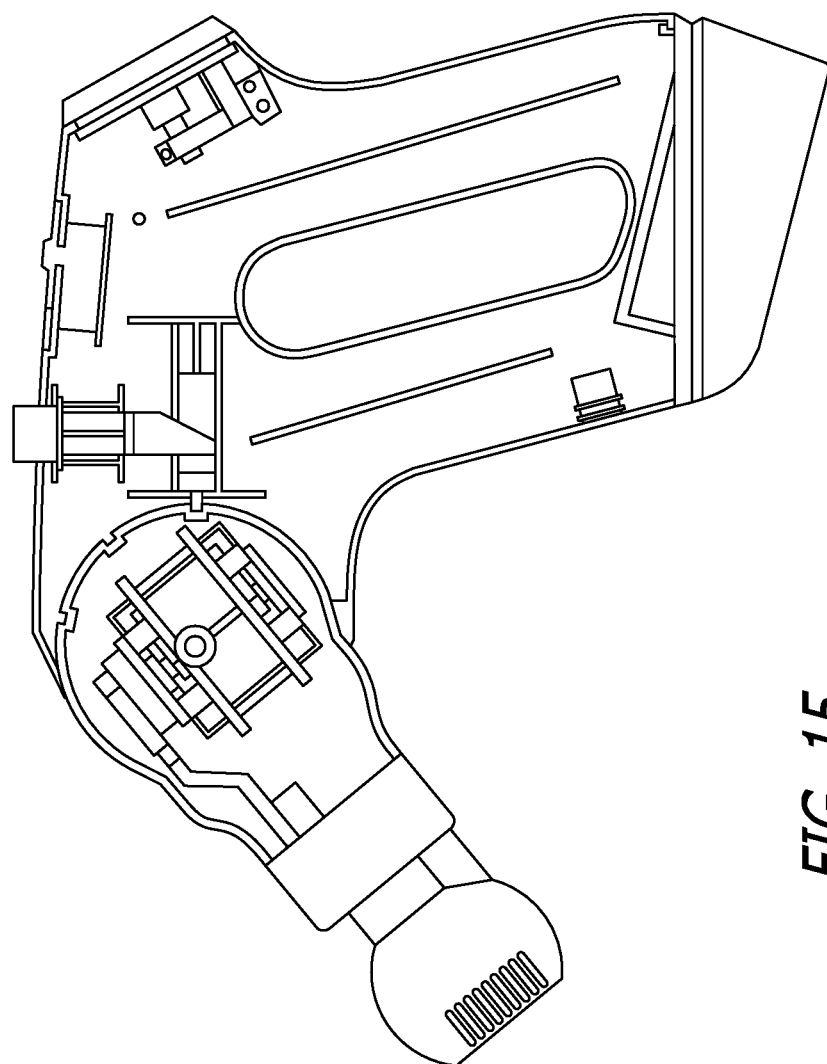
FIG. 15 displays another embodiment of the present invention. This is a sectional view of the physical therapy device in which the front angle of the head housing shell has been adjusted downward.

FIG. 15 displays another embodiment of the present invention. This is a sectional view of the physical therapy device in which the front angle of the head housing shell has been adjusted downward. The motor is in the head housing shell, instead of the main housing shell. Therefore, the whole head housing shell, instead of part of it, can be adjusted downward.

FIG. 16

Figure 16:
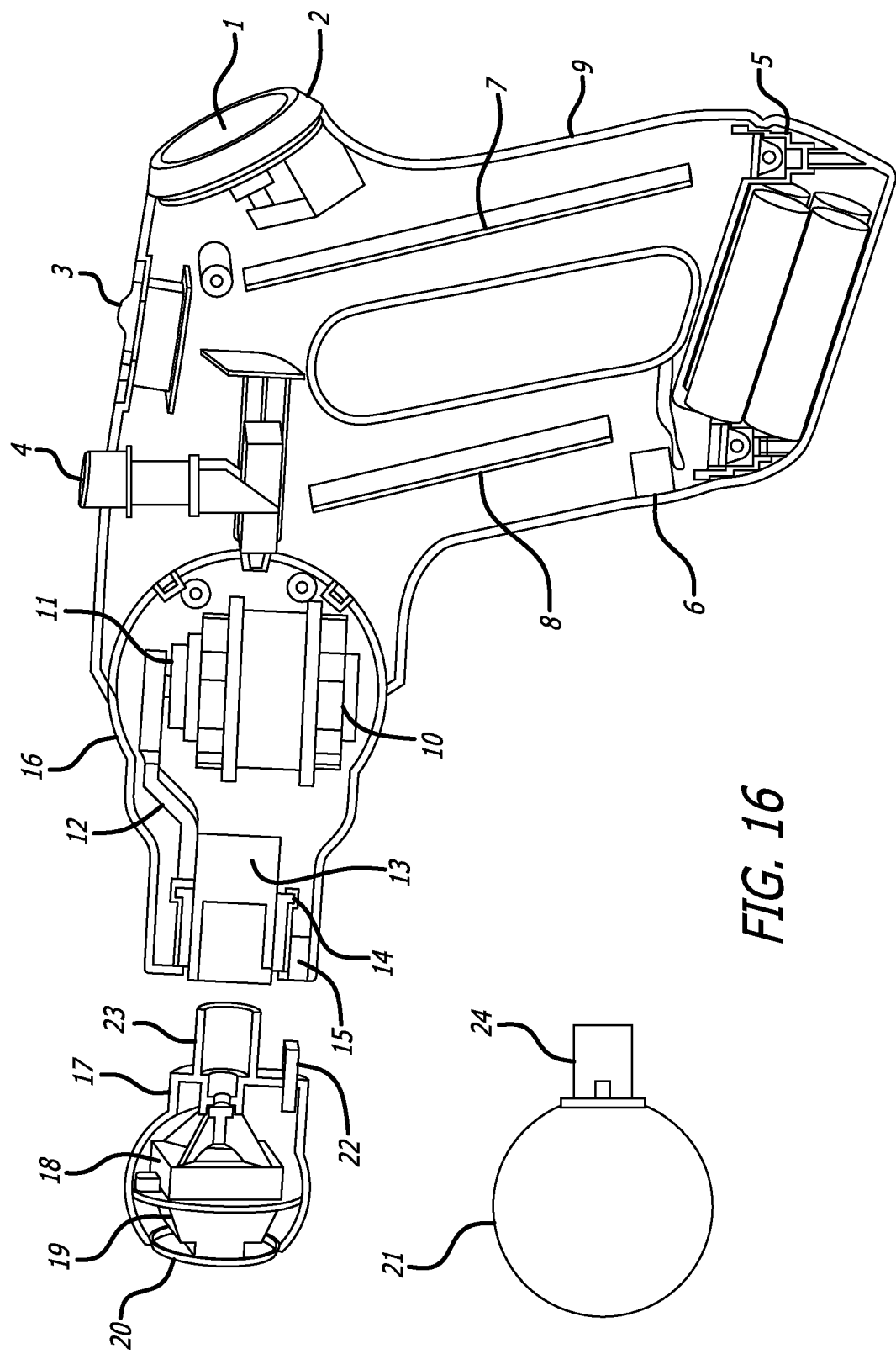
FIG. 16 displays another embodiment of the present invention. This is a display of all the internal parts of the physical therapy device.

FIG. 16 displays another embodiment of the present invention. Display 1 is where information is displayed relevant to the mode and intensity that the user has set the device to. Knob for intensity adjustment 2 is where the intensity can be changed, either for percussion, cooling or heating purposes. On/off switch for percussion, cooling and heating 3 is used to switch the device on or off, as well as to change between the 3 different modes: percussion, cooling and heating. Button for head angle adjustment 4 allows the front piece to be adjusted at either an upward or downward angle. Battery 5 is what powers the invention, and is removable if necessary. Battery charging port 6 is where a plug can be inserted in order to charge the battery, and the battery can also be removed and charged in a separate charging station. IC (integrated circuit) board for the intensity adjustment 7 is the electronic circuit board that controls the adjustments of intensity for 3 different mode purposes: percussion, cooling and heating. IC board for the motor control 8 is the electronic circuit board that controls the motion of the invention in the various modes, such that it vibrates at the correct intensity/speed. Main housing shell 9 is the body cover that contains the different parts of the invention, except for the battery 5 because it is removable, the head housing shell 16, the heating/cooling attachment 20 and the percussion attachment 21. Motor 10 is what provides the driving force to perform the percussion of the invention.

Eccentric wheel 11 is a circular disk solidly fixed to the rotating axle of Motor 10. The axle on the other side of the eccentric wheel 11 is off the center, and connects to the connecting rod 12. The connecting rod 12 connects to the pushing rod 13, so the motor 10 can provide the percussion force to the pushing rod 13. The Pushing rod 13 makes a back and forth percussion.

Bushing 14 is used to provide the supportive direction and even cushion/protection to the pushing rod 13. Since the pushing rod 13 is constantly moving back and forth to provide percussion, the pushing rod 13 needs a supportive direction and even cushion/protection from damage and wear and tear. As such, the bushing 14 is able to provide a supportive direction and even cushion/protection that helps to direct and preserve the pushing rod 13.

Contact slot for heating/cooling 15 is where Heating/Cooling attachment 20 connects to the invention through conductive contact for the heating/cooling attachment 22. Therefore, the invention could provide the power to the Heating/Cooling attachment 20 for heating/cooling.

Head housing shell 16 contains all the parts that are within the head of the invention. The head housing shell 16 also has the capability to adjust its front angle upwards or downwards. This can be helpful for a user's comfort in case the user has difficulty in moving in certain ways. The motor 10 is in the head housing shell 16, instead of the main housing shell 9. Therefore, the whole head housing shell 16, instead of part of it, can be adjusted upward or downward. Moreover, the motor 10 located in the head housing shell 16 can shorten the connection of motor 10 to the pushing rod 13 that constantly moves back and forth to provide percussion to the heating/cooling attachment 20 or the percussion attachment 21. Therefore, the present invention can potentially reduce use of parts and their length between the motor 10 and the pushing rod 13, and reduce the amount of noise emitted into the workplace or environment from the mechanical connection between the motor 10 and the pushing rod 13.

Housing shell for heating/cooling attachment 17 contains all the parts of the Heating/Cooling attachment 20.

Cooling vent/fan 18 provides the cooling function that is activated in the cooling mode of the invention.

Heating/Cooling component 19 is an integrated circuit of a heating/cooling semiconductor and related elements to control the functioning and intensity of the heating mode and cooling mode, based on the user's adjustments on the knob for intensity adjustment 2.

Heating/Cooling attachment 20 is seen separated from the rest of the invention, and could be fastened to the invention through fastening contact for the heating/cooling attachment 23, because it can be removed and reattached, i.e. it is reattachable. In one embodiment of the present invention, the heating/cooling attachment 20 is in the shape of a semi-sphere or other shapes.

The housing shell for the heating/cooling attachment 17 is made of plastic, foam, or metal, or any combination of plastic, foam and metal. The front part of the heating/cooling attachment 20 is made of metal that has the capability to be in contact with human skin.

Percussion attachment 21 is seen as a separate part from the rest of the invention, and could be fastened to the invention through fastening contact for the percussion attachment 24, because it can be removed and reattached, i.e. it is reattachable. In one embodiment of the present invention, the percussion attachment 21 is made of plastic, foam, mental, or any combination of plastic, foam and metal. In another embodiment of the present invention, the percussion attachment 21 is in the shape of a sphere or other shapes.

In another embodiment of the present invention, before a user can use the present invention, the user needs to install the battery 5 onto the bottom of the device. If needed, the user could charge the battery 5 through the charging port 6 or in the separate charging station. Then, the user should attach the percussion attachment 21 onto the front of the device through the fastening contact 24. Except for the percussion attachment 21 and the battery 5, the remaining parts/components are mounted inside the main housing shell 9 and the head housing shell 16.

Also, the user could use the button 4 to adjust the angle of the head of the device for his/her preference. After switching the On/off switch for percussion, cooling and heating 3 to the Percussion position, the device is turned on and is at the Percussion mode, which is reflected on the display 1. The user could use the knob for intensity adjustment 2 to adjust the percussion intensity/speed to a desired intensity/speed that is connected to the IC board for the intensity adjustment 7.

Afterward, the user could place the percussion attachment 21 onto the user's skin for the percussion. The back and forth percussion of the percussion attachment 21 is realized by the pushing rod 13. The bushing 14 supportively directs and protects the pushing rod 13. The pushing rod 13 is connected to the motor 10 through the connecting rod 12 and the eccentric wheel 11. The IC board for the motor control 8 will convert the power of the battery 5 to the motor 10. Therefore, the user could feel the back and forth percussion on the user's skin from the device.

In addition to the percussion alone, the user could experience the heating/cooling from the device: before use, the user needs to install the battery 5 onto the bottom of the device (if needed, the user could charge the battery through the charging port 6 or in the separate charging station), and attach the heating/cooling attachment 20 onto the front of the device through the fastening contact 23 and the conductive contact for the heating/cooling attachment 22 that is inserted into the contact slot for heating/cooling 15. Except for the heating/cooling attachment 20 and the battery 5, the remaining parts/components are mounted inside the main housing shell 9 and the head housing shell 16. The cooling vent/fan 18 and the heating/cooling component 19 are mounted into the housing shell for the heating/cooling attachment 17. Also, the user could use the button 4 to adjust the angle of the head of the device for his/her preference. After switching the on/off switch 3 to the heating or cooling position, the device is turned on and is in the heating or cooling mode, which is reflected on the display 1. The user could use the knob for intensity adjustment 2 to adjust the heating or cooling temperature to a desired temperature that is connected to the IC board for the intensity adjustment 7.

Afterward, the user could place the heating/cooling attachment 20 onto the user's skin for heating or cooling, and the default percussion in the heating/cooling mode is 1200 rpm (20 Hz). The back and forth percussion of the heating/cooling attachment 20 is realized by the pushing rod 13. The bushing 14 supportively directs and protects the pushing rod 13. The pushing rod 13 is connected to the motor 10 through the connecting rod 12 and the eccentric wheel 11. The IC board for the motor control 8 will convert the power of the battery 5 to the motor 10. Therefore, the user could feel the heating or cooling together with the back and forth percussion on the user's skin from the device.

FIG. 17

Figure 17:
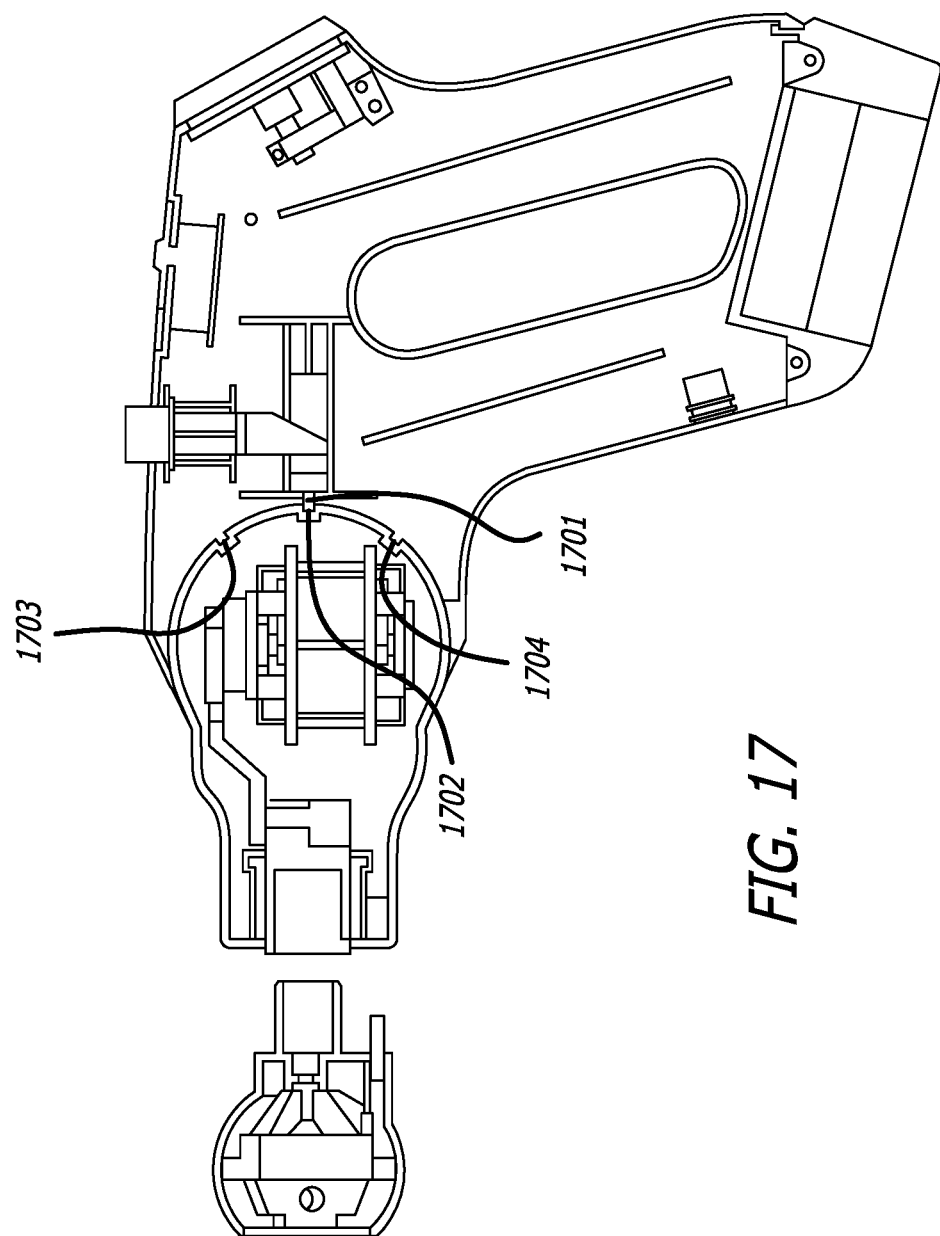
FIG. 17 displays another embodiment of the present invention. Here, the internal parts of the invention that allow the head housing shell to rotate up or down are displayed.

FIG. 17 displays another embodiment of the present invention. Here, the internal parts of the invention that allow the whole head housing shell to rotate up or down are displayed. Lock pin 1701 locks the head housing shell into one of the three lock slots 1702, 1703 and 1704. Lock slot 1702 allows the head housing shell to face directly forward, at a horizontal angle of 0 degrees. Lock slot 1703 allows the head housing shell to face upward-left at a 40-45 degree angle positively horizontally. Lock slot 1704 allows the head housing shell to face downward-left at a 40-45 degree angle negatively horizontally.

FIG. 18

Figure 18:
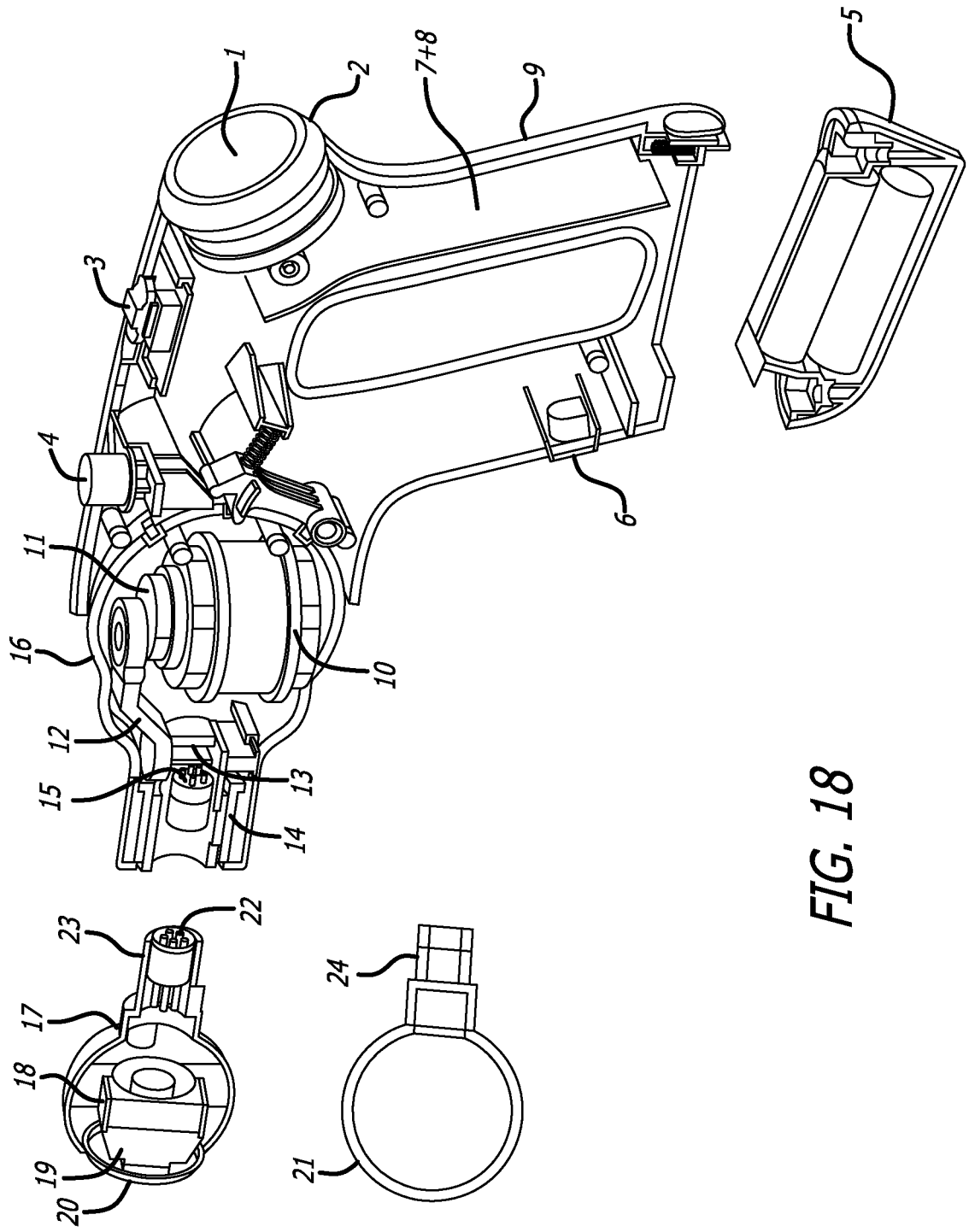
FIG. 18 displays another embodiment of the present invention. This is a display of all the internal parts of the physical therapy device.

FIG. 18 displays another embodiment of the present invention. Display 1 is where information is displayed relevant to the mode and intensity that the user has set the device to. Knob for intensity adjustment 2 is where the intensity can be changed, either for percussion, cooling or heating purposes. On/off switch for percussion, cooling and heating 3 is used to switch the device on or off, as well as to change between the 3 different modes: percussion, cooling and heating. Button for head angle adjustment 4 allows the front piece to be adjusted at either an upward or downward angle. Battery 5 is what powers the invention, and is removable if necessary. Battery charging port 6 is where a plug can be inserted in order to charge the battery. IC board for the intensity adjustment and motor control 7+8 is the combination of the following two electronic circuit boards: A circuit board that controls the adjustments of intensity for 3 different purposes: percussion, cooling and heating, and a circuit board that controls the motion of the invention in the various modes, such that it vibrates at the correct intensity/speed. Main housing shell 9 is the body that contains the different parts of the invention, except for the battery 5 because it is removable, the head housing shell 16, the heating/cooling attachment 20 and the percussion attachment 21. Motor 10 is what provides the driving force to perform the percussion of the invention. Eccentric wheel 11 is a circular disk solidly fixed to the rotating axle of Motor 10. The axle on the other side of the eccentric wheel 11 is off the center, and connects to the connecting rod 12. The connecting rod 12 connects to the pushing rod 13, so the motor can provide the percussion force to the pushing rod 13. The pushing rod 13 makes a back and forth percussion.

The bushing 14 is used to provide the supportive direction and even cushion/protection to the pushing rod 13. Since the pushing rod 13 is constantly moving back and forth to provide percussion, the pushing rod 13 needs a supportive direction and even cushion/protection from damage and wear and tear. As such, the bushing 14 is able to provide a supportive direction and even cushion/protection that helps to direct and preserve the pushing rod 13.

Contact slot for heating/cooling 15 is where the Heating/Cooling attachment 20 connects to the invention through conductive contact for the heating/cooling attachment 22. Therefore, the invention could provide the power to the Heating/Cooling attachment 20 for heating/cooling.

Head housing shell 16 contains all the parts that are within the head of the invention. The head housing shell 16 also has the capability to adjust its front angle upwards or downwards. This can be helpful for a user's comfort in case the user has difficulty in moving in certain ways. The motor 10 is in the head housing shell 16, instead of the main housing shell 9. Therefore, the whole head housing shell 16, instead of part of it, can be adjusted upward or downward. Moreover, the motor 10 located in the head housing shell 16 can shorten the connection of motor 10 to the pushing rod 13 that constantly moves back and forth to provide percussion to the heating/cooling attachment 20 or the percussion attachment 21. Therefore, the present invention can potentially reduce use of parts and their length between the motor 10 and the pushing rod 13, and reduce the amount of noise emitted into the workplace or environment from the mechanical connection between the motor 10 and the pushing rod 13.

Housing shell for heating/cooling attachment 17 contains all the parts of the Heating/Cooling attachment 20.

Cooling vent/fan 18 provides the cooling function that is activated in the cooling mode of the invention.

Heating/Cooling component 19 is an integrated circuit of a heating/cooling semiconductor and related elements to control the functioning and intensity of heating mode and cooling mode, based on the user's adjustments on the knob for intensity adjustment 2.

Heating/Cooling attachment 20 is seen separated from the rest of the invention, and could be fastened to the invention through the fastening contact for the heating/cooling attachment 23, because it can be removed and reattached, i.e. it is reattachable. In one embodiment of the present invention, the heating/cooling attachment 20 is in the shape of a semi-sphere or other shapes.

The housing shell for the heating/cooling attachment 17 is made of plastic, foam, or metal, or any combination of plastic, foam and metal. The front part of the heating/cooling attachment 20 is made of metal that has the capability to be in contact with human skin.

Percussion attachment 21 is seen as a separate part from the rest of the invention, and could be fastened to the invention through the fastening contact for the percussion attachment 24, because it can be removed and reattached, i.e. it is reattachable. In one embodiment of the present invention, the percussion attachment is made of plastic, foam, mental, or any combination of plastic, foam and metal. In another embodiment of the present invention, the percussion attachment is in the shape of a sphere or other shapes.

In another embodiment of the present invention, before a user can use the present invention, the user needs to install the battery 5 onto the bottom of the device. If needed, the user could charge the battery 5 through the charging port 6 or in the separate charging station. Then, the user should attach the percussion attachment 21 onto the front of the device through the fastening contact 24. Except for the percussion attachment 21 and the battery 5, the remaining parts/components are mounted inside the main housing shell 9 and the head housing shell 16.

Also, the user could use the button 4 to adjust the angle of the head of the device for his/her preference. After switching the On/off switch for percussion, cooling and heating 3 to the percussion position, the device is turned on and is at the percussion mode, which is reflected on the display 1. The user could use the knob for intensity adjustment 2 to adjust the percussion intensity/speed to a desired intensity/speed that is connected to the IC board for the intensity adjustment and motor control 7+8.

Afterward, the user could place the percussion attachment 21 onto the user's skin for the percussion. The back and forth percussion of the percussion attachment 21 is realized by the pushing rod 13. The bushing 14 supportively directs and protects the pushing rod 13. The pushing rod 13 is connected to the motor 10 through the connecting rod 12 and the eccentric wheel 11. The IC board for the intensity adjustment and motor control 7+8 will convert the power of the battery 5 to the motor 10. Therefore, the user could feel the back and forth percussion on the user's skin from the device.

In addition to the percussion alone, the user could experience the heating/cooling from the device: before use, the user needs to install the battery 5 onto the bottom of the device (if needed, the user could charge the battery through the charging port 6 or in the separate charging station), and attach the heating/cooling attachment 20 onto the front of the device through the fastening contact for the heating/cooling attachment 23 and the conductive contact for the heating/cooling attachment 22 that is inserted into the contact slot for heating/cooling 15. Except for the heating/cooling attachment 20 and the battery 5, the remaining parts/components are mounted inside the main housing shell 9 and the head housing shell 16. The cooling vent/fan 18 and the heating/cooling component 19 are mounted into the housing shell for heating/cooling attachment 17. Also, the user could use the button 4 to adjust the angle of the head of the device for his/her preference. After switching the on/off switch 3 to the heating or cooling position, the device is turned on and is in the heating or cooling mode, which is reflected on the display 1. The user could use the knob for intensity adjustment 2 to adjust the heating or cooling temperature to a desired temperature that is connected to the IC board for the intensity adjustment and motor control 7+8.

Afterward, the user could place the heating/cooling attachment 20 onto the user's skin for heating or cooling, and the default percussion in the heating/cooling mode is 1200 rpm (20 Hz). The back and forth percussion of the heating/cooling attachment 20 is realized by the pushing rod 13. The bushing 14 supportively directs and protects the pushing rod 13. The pushing rod 13 is connected to the motor 10 through the connecting rod 12 and the eccentric wheel 11. The IC board for the intensity adjustment and motor control 7+8 will convert the power of the battery 5 to the motor 10. Therefore, the user could feel the heating or cooling together with the back and forth percussion on the user's skin from the device.

FIG. 19

Figure 19:
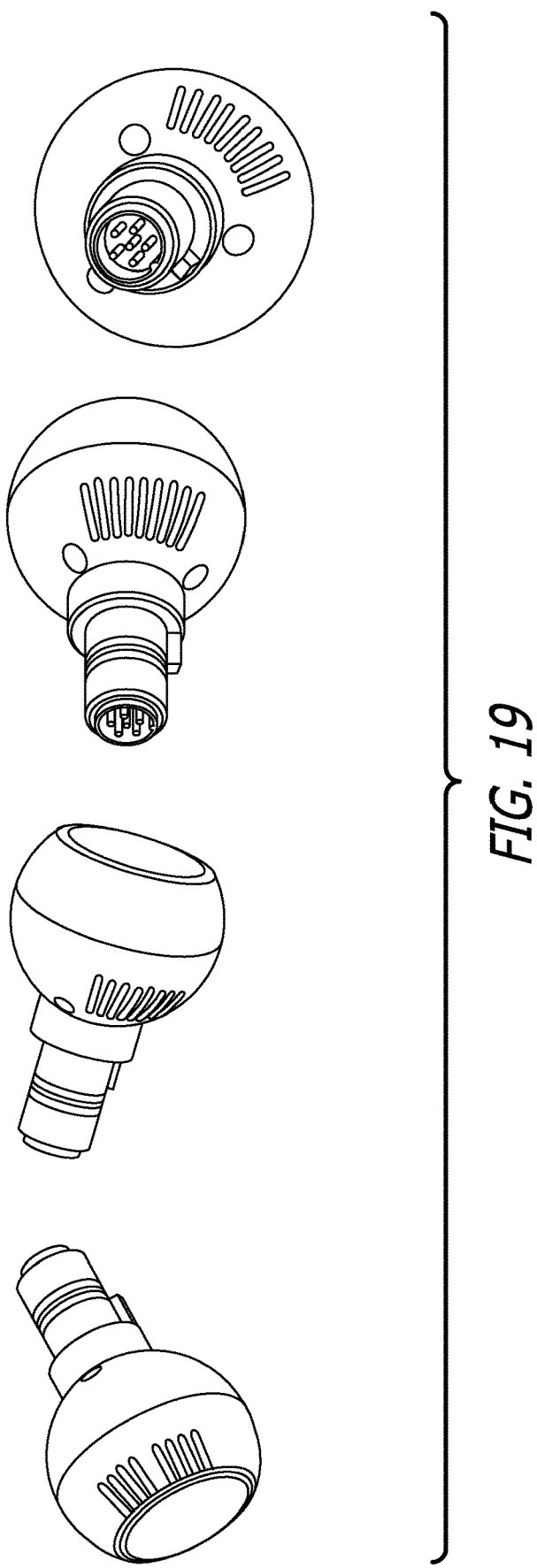
FIG. 19 displays another embodiment of the present invention. This shows different views of the heating/cooling attachment that is attached and detached to the physical therapy device.

FIG. 19 displays another embodiment of the present invention. This shows different views of the heating/cooling attachment that is attached and detached to the physical therapy device.

FIG. 20

Figure 20:
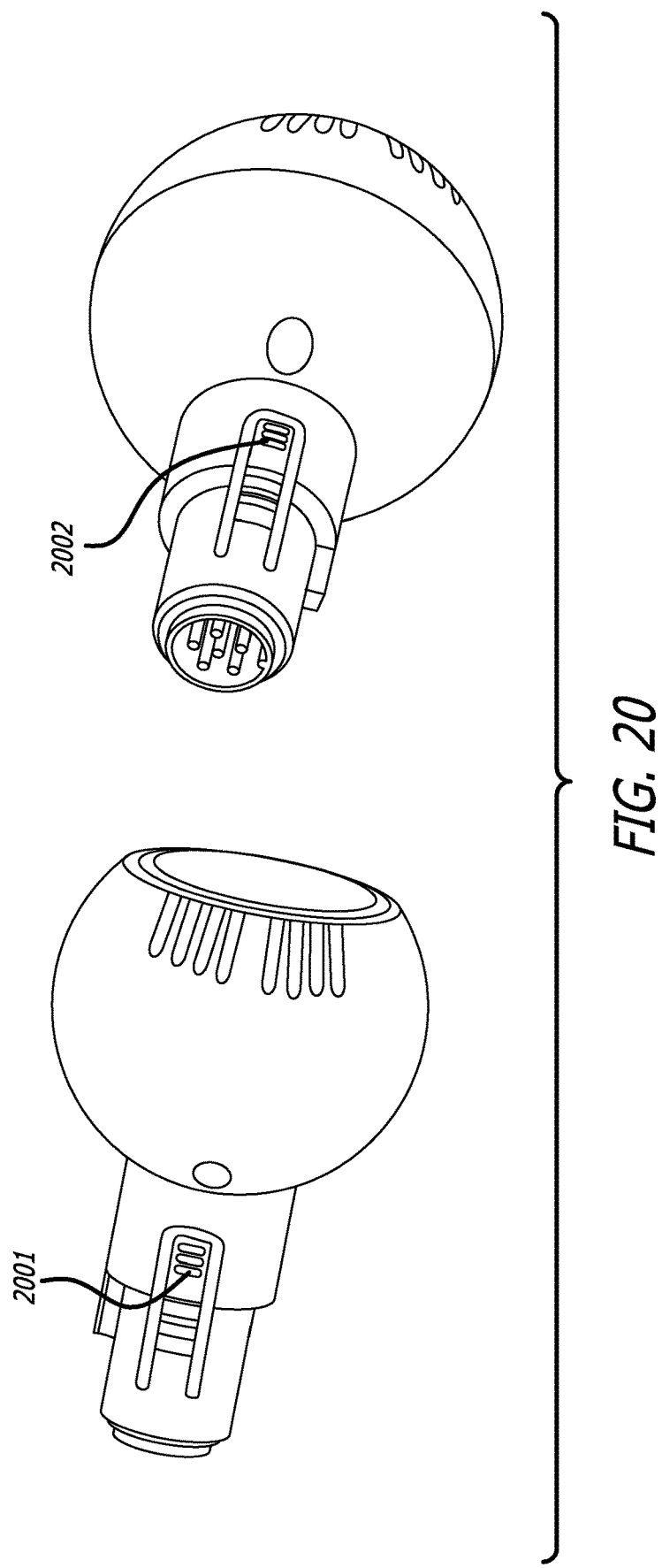
FIG. 20 displays another embodiment of the present invention. This shows different views of the heating/cooling attachment with lock pins, so the lock pins can further secure the connection between the heating/cooling attachment and the device.

FIG. 20 displays another embodiment of the present invention. This shows different views of the heating/cooling attachment with lock pins 2001 and 2002 on its both sides, so the lock pins can secure the connection between the heating/cooling attachment and the device.

FIG. 21

Figure 21:
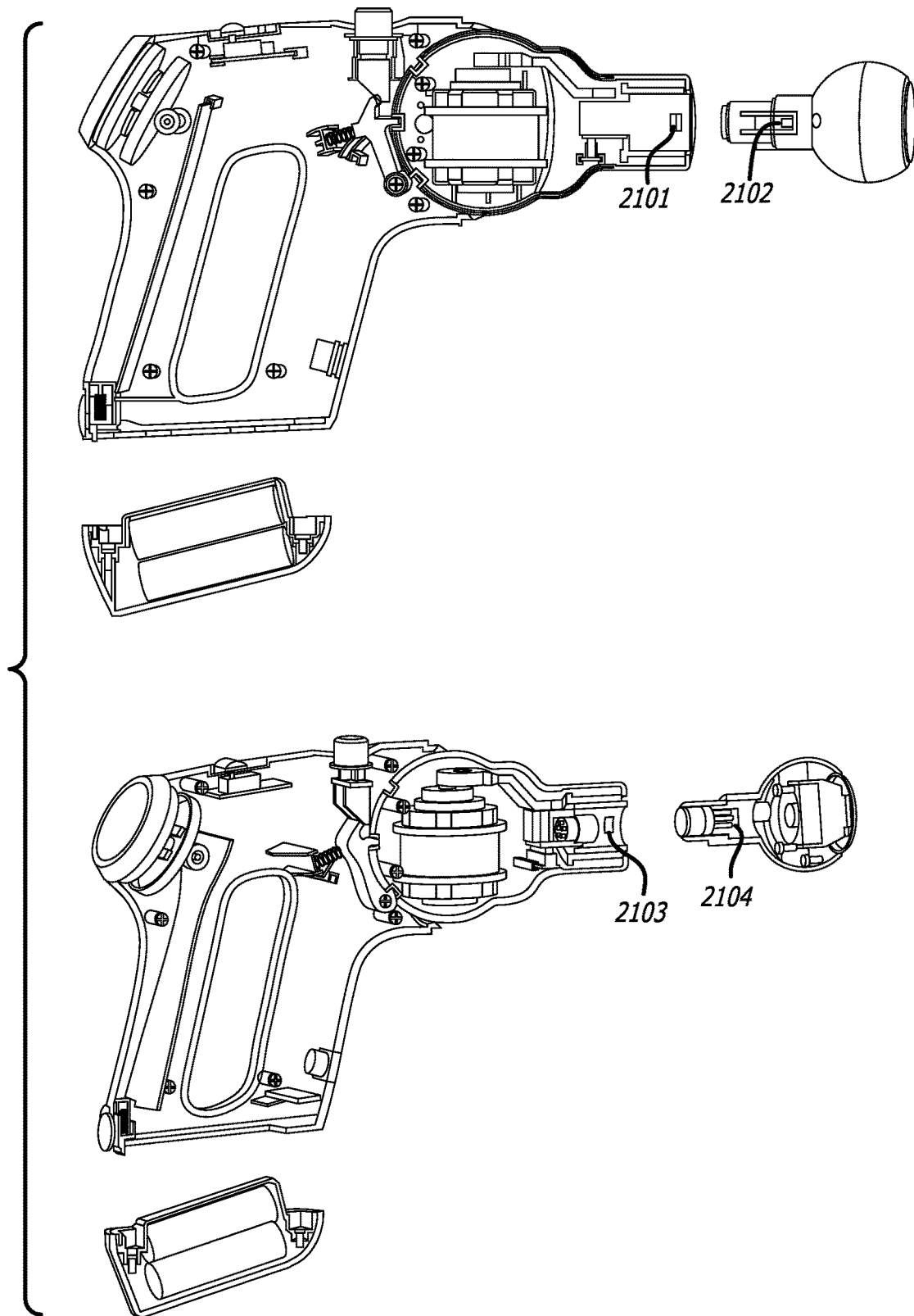
FIG. 21 displays another embodiment of the present invention. This shows lock slots in the device and lock pins on the heating/cooling attachment, so the heating/cooling attachment can be secured in place.

FIG. 21 displays another embodiment of the present invention. Here, there are a lock slot 2101 and a lock slot 2103, which are respectively in the left side and the right side of the head housing shell of the physical therapy device. There are also a lock pin 2102 and a lock pin 2104, which are respectively on the left side and the right side of the heating/cooling attachment. The lock pins 2102 and 2104 connect to the lock slots 2101 and 2103, respectively, so the connection is secured between the heating/cooling attachment and the device.

The physical therapy device moves in a back and forth percussion at a high speed. As such, it is useful to add the lock slot and lock pin between the physical therapy device and the heating/cooling attachment. Therefore, the heating/cooling attachment can remain in place during the high-speed percussion, which is critical for the user's safety.

FIG. 22

Figure 22:
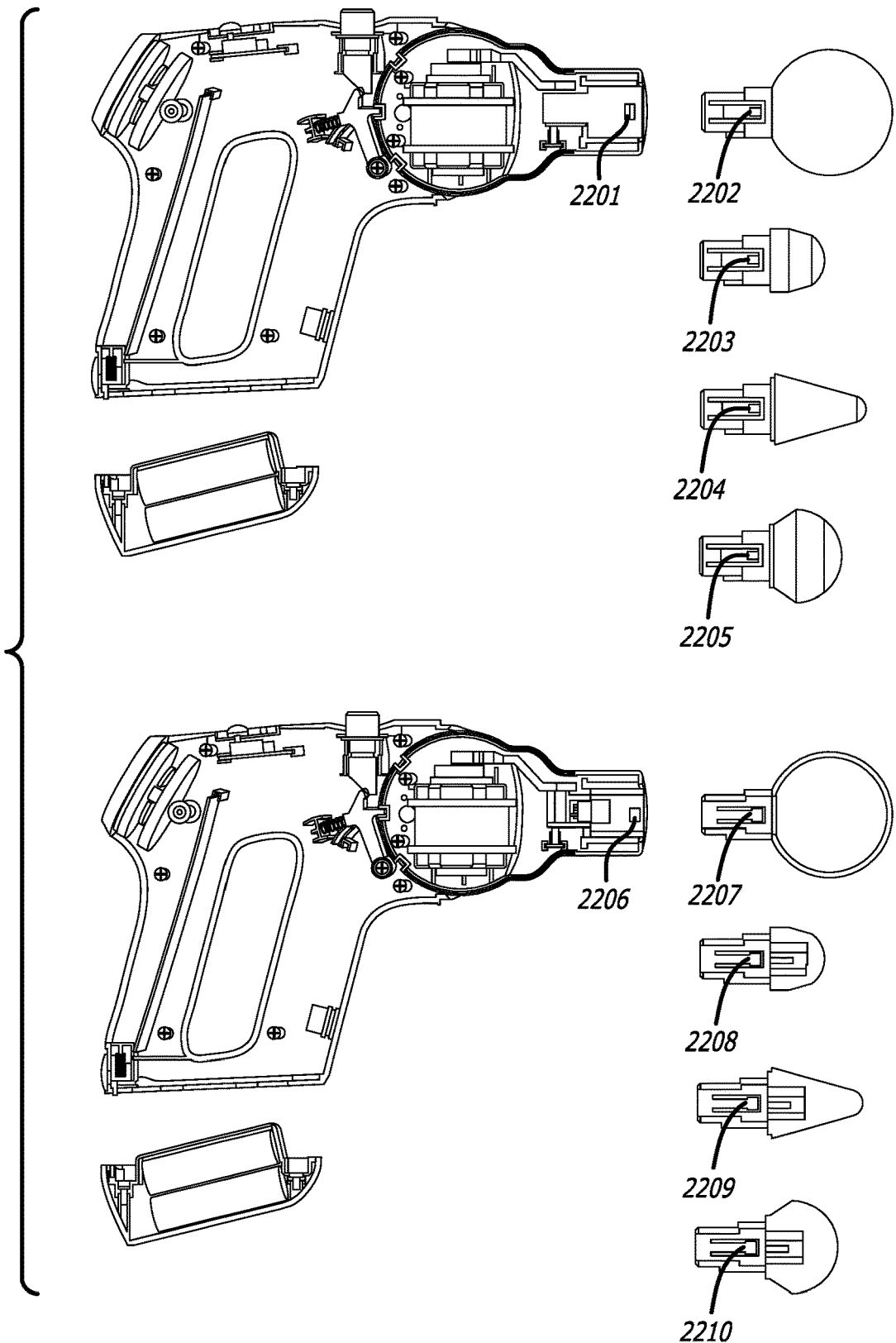
FIG. 22 displays another embodiment of the present invention. This shows lock slots in the device and lock pins on each percussion attachment, so each percussion attachment can be secured in place.

FIG. 22 displays another embodiment of the present invention. Here, there are a lock slot 2201 and a lock slot 2206, which are respectively in the left side and the right side of the head housing shell of the physical therapy device. Also, there are a lock pin 2202 and a lock pin 2207, which are respectively on the left side and the right side of the percussion attachment; there are a lock pin 2203 and a lock pin 2208, which are respectively on the left side and the right side of the first alternative percussion attachment; there are a lock pin 2204 and a lock pin 2209, which are respectively on the left side and the right side of the second alternative percussion attachment; there are a lock pin 2205 and a lock pin 2210, which are respectively on the left side and the right side of the third alternative percussion attachment.

The physical therapy device moves in a back and forth percussion at a very high speed when connected to the percussion attachment. As such, it is useful to add the lock slot and lock pin between the physical therapy device and the percussion attachment. Therefore, the percussion attachment can remain in place during the high-speed percussion, which is critical for the user's safety. This is a unique configuration that provides more stability than anything else on the market.

FIG. 23

Figure 23:
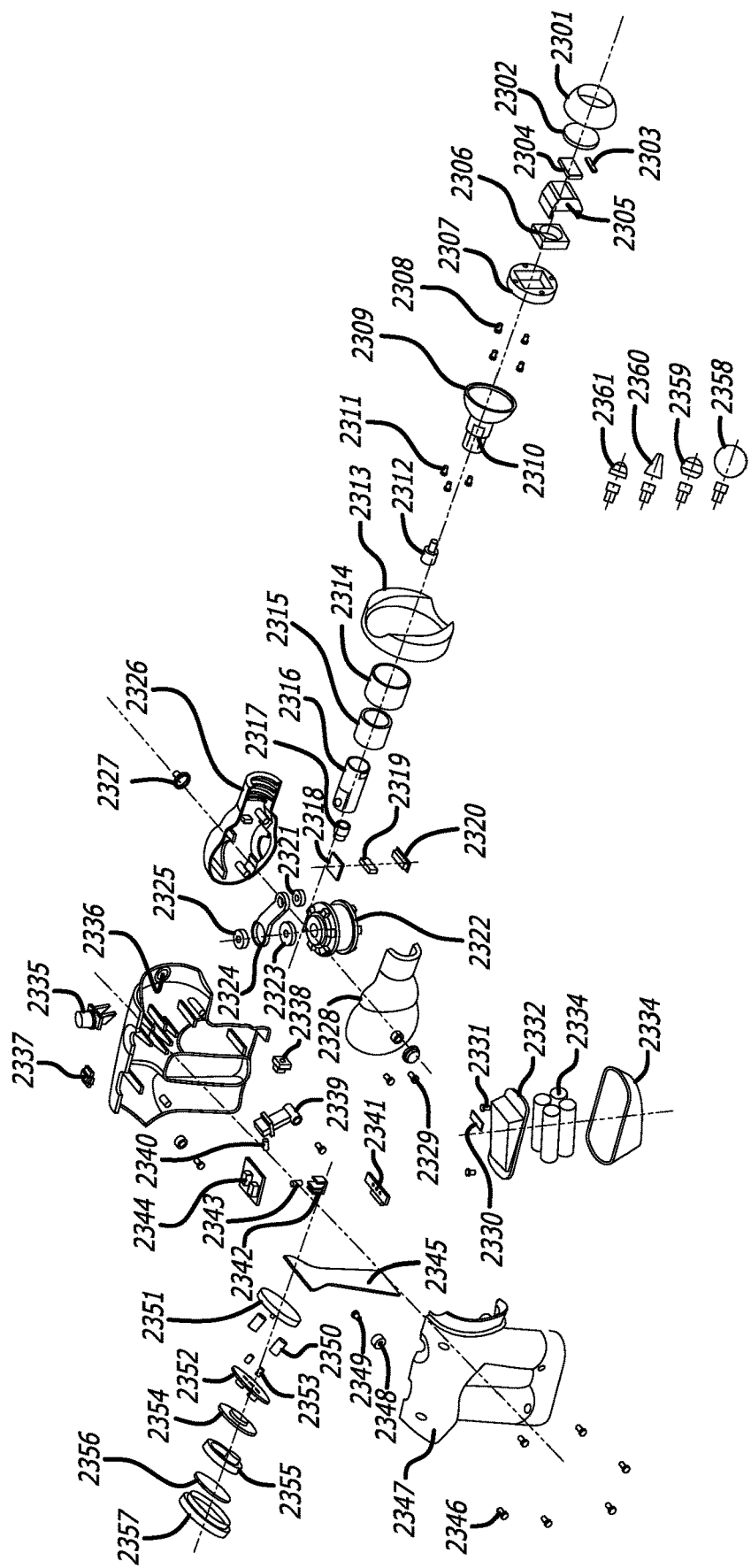
FIG. 23 displays another embodiment of the present invention. Here, the physical therapy device is shown in a disassembled view, so each internal part can be seen.

FIG. 23 displays another embodiment of the present invention. Here the physical therapy device is shown in a disassembled view, so each internal part can be seen.

The parts include Lower shell of the heating/cooling attachment 2301, Metal contact to skin 2302, Temperature sensor 2303, Heating/cooling semiconductor 2304, Heat sink 2305, Vent/fan 2306, Vent/fan stand 2307, Screws 2308, Upper shell of the heating/cooling attachment 2309 with or without the lock pin 2310, Screws 2311, Plugin pin piece 2312, Fastening ring of the main housing shell 2313, Bushing cushion 2314, Bushing 2315, Pushing rod 2316, Plugin jack piece 2317, Contact slice 2318, Carbon brush 2319, Carbon brush stand 2320. Minor bearing 2321, Motor 2322, Eccentric wheel 2323, Connecting rod 2324, Major bearing 2325, Upper head housing shell 2326, Positioning cap of the head housing shell 2327, Lower head housing shell 2328, Screws 2329, Contact slice of battery 2330, Screws 2331, Upper shell of battery 2332, Battery 2333, Lower shell of battery 2334, Button for head angle adjustment 2335, Upper main housing shell 2336, On/Off switch for percussion, cooling, and heating 2337, Battery charging port 2338, Lock pin for head angle adjustment 2339, Lock pin spring for head angle adjustment 2340, Conductive contact for contact slice of battery 2341, Lock button for battery 2342, Lock spring for battery 2343, Contact for percussion, cooling, and heating 2344, IC board for the intensity adjustment and motor control 2345, Screws 2346, Lower main housing shell 2347, Direction gear of knob for intensity adjustment 2348, Screw 2349, Transmission gear of knob for intensity adjustment 2350, Rotation gear of knob for intensity adjustment 2351, Gear stand of knob for intensity adjustment 2352, Screws 2353, Coding IC board 2354, Display 2355, Display glass 2356, Knob for intensity adjustment 2357, the percussion attachment 2358, the first alternative percussion attachment 2359, the second alternative percussion attachment 2360, and the third alternative percussion attachment 2361.

All of these parts fit together as seen in FIG. 23.

A system to provide physical therapy in the form of heating, cooling and/or percussion, comprising: a device that contains a battery, a motor, a knob for adjustment of speed or intensity, a button for angle adjustment of the front of the device, and a switch to turn the device on or off or put the device in heating mode or put the device in cooling mode or put the device in percussion mode; wherein the device contains a motor and a pushing rod that supply the movement that results in percussion of a removable heating/cooling attachment and a removable percussion attachment; wherein the front of the device connects to the removable heating/cooling attachment that contains an electronic component to control heating or cooling and a cooling fan; wherein the removable heating/cooling attachment can be used for heating or cooling; wherein a housing shell for the heating/cooling attachment is made of plastic, foam, or metal, or any combination of plastic, foam and metal; wherein the front part of the heating/cooling attachment is made of metal that has the capability to be in contact with human skin in order to provide either heating or cooling at fixed or adjusted degrees that are optimal for physical therapy and/or blood circulation; wherein the removable heating/cooling attachment can be replaced by the removable percussion attachment that is used for percussion; wherein the removable percussion attachment can be placed on the skin of a user in order to provide percussion massage therapy at fixed or adjusted speeds that are optimal for physical therapy.

The system further comprising: wherein the device contains a removable battery on the bottom of the device; wherein the device contains a knob for adjustment of speed or intensity, and a button for angle adjustment of the front of the device.

The system further comprising: wherein the removable heating/cooling attachment provides cooling at the fixed or adjusted temperatures of 6 degrees Celsius, 5 degrees Celsius, 4 degrees Celsius, 3 degrees Celsius, and 2 degrees Celsius.

The system further comprising: wherein the removable heating/cooling attachment also provides cooling through the clothing of the user at the fixed or adjusted temperatures of 1 degree Celsius, and 0 degrees Celsius.

The system further comprising: wherein the removable heating/cooling attachment provides heating at the fixed or adjusted degrees of 40 degrees Celsius, 41 degrees Celsius, 42 degrees Celsius, 43 degrees Celsius, and 44 degrees Celsius.

The system further comprising: wherein the removable heating/cooling attachment also provides heating through the clothing of the user at the fixed or adjusted temperatures of 45 degrees Celsius through 75 degrees Celsius at 1 degree increments.

The system further comprising: wherein the removable percussion attachment provides percussion at the fixed or adjusted speeds of 1200 rpm or 20 Hz, 1800 rpm or 30 Hz, 2400 rpm or 40 Hz, 3300 rpm or 55 Hz, 3900 rpm or 65 Hz.

The system further comprising: wherein the removable percussion attachment also provides percussion at the fixed or adjusted speeds of 900 rpm or 15 Hz, 4500 rpm or 75 Hz, 5100 rpm or 85 Hz, 5700 rpm or 95 Hz, and 6000 rpm or 100 Hz.

The system further comprising: wherein the removable percussion attachment is made of plastic, foam, or metal or of any combination of plastic, foam and metal.

The system further comprising: wherein the device contains a removable battery on the bottom of the device; wherein the removable heating/cooling attachment provides cooling at the fixed or adjusted degrees of 6 degrees Celsius, 5 degrees Celsius, 4 degrees Celsius, 3 degrees Celsius, and 2 degrees Celsius; wherein the removable heating/cooling attachment also provides cooling through the clothing of the user at the fixed or adjusted temperatures of 1 degree Celsius, and 0 degrees Celsius; wherein the removable heating/cooling attachment provides heating at the fixed or adjusted degrees of 40 degrees Celsius, 41 degrees Celsius, 42 degrees Celsius, 43 degrees Celsius, and 44 degrees Celsius; wherein the removable heating/cooling attachment also provides heating through the clothing of the user at the fixed or adjusted temperatures of 45 degrees Celsius through 75 degrees Celsius at 1 degree increments; wherein the removable percussion attachment provides percussion at the fixed or adjusted speeds of 1200 rpm or 20 Hz, 1800 rpm or 30 Hz, 2400 rpm or 40 Hz, 3300 rpm or 55 Hz, 3900 rpm or 65 Hz; wherein the removable percussion attachment also provides percussion at the fixed or adjusted speeds of 900 rpm or 15 Hz, 4500 rpm or 75 Hz, 5100 rpm or 85 Hz, 5700 rpm or 95 Hz, and 6000 rpm or 100 Hz; wherein the removable percussion attachment is made of plastic, foam, metal, or any combination of plastic, foam and metal; wherein back and forth percussion of the percussion attachment is realized by a pushing rod; wherein a bushing supportively directs and protects the pushing rod; wherein the pushing rod is connected to a motor through a connecting rod and an eccentric wheel; wherein an Integrated Circuit board for motor control will convert the power of a battery to the motor; wherein the user feels the back and forth percussion on the user's skin from the device.

A method to provide physical therapy in the form of heating, cooling and/or percussion, comprising: a device that contains a battery, a motor, and a switch to turn the device on or off or put the device in heating mode or put the device in cooling mode or put the device in percussion mode; wherein the device contains a motor and a pushing rod that supply the movement that results in percussion of a removable heating/cooling attachment and a removable percussion attachment; wherein the front of the device connects to the removable heating/cooling attachment that contains an electronic component to control heating or cooling and a cooling fan; wherein the removable heating/cooling attachment can be used for heating or cooling; wherein a housing shell for the heating/cooling attachment is made of plastic, foam, or metal, or any combination of plastic, foam and metal; wherein the front part of the heating/cooling attachment is made of metal that has the capability to be in contact with human skin in order to provide either heating or cooling at fixed or adjusted degrees that are optimal for physical therapy and/or blood circulation; wherein the removable heating/cooling attachment can be replaced by the removable percussion attachment that is used for percussion; wherein the removable percussion attachment can be placed on the skin of a user in order to provide percussion therapy at fixed or adjusted speeds that are optimal for physical therapy.

The method further comprising: wherein the device contains a removable battery on the bottom of the device; wherein the device contains a knob for adjustment of speed or intensity, and a button for angle adjustment of the front of the device.

The method further comprising: wherein the removable heating/cooling attachment provides cooling at the fixed or adjusted degrees of 6 degrees Celsius, 5 degrees Celsius, 4 degrees Celsius, 3 degrees Celsius, and 2 degrees Celsius; wherein the removable heating/cooling attachment also provides cooling through the clothing of the user at the fixed or adjusted temperatures of 1 degree Celsius, and 0 degrees Celsius.

The method further comprising: wherein the removable heating/cooling attachment provides heating at the fixed or adjusted degrees of 40 degrees Celsius, 41 degrees Celsius, 42 degrees Celsius, 43 degrees Celsius, and 44 degrees Celsius; wherein the removable heating/cooling attachment also provides heating through the clothing of the user at the fixed or adjusted temperatures of 45 degrees Celsius through 75 degrees Celsius at 1 degree increments.

The method further comprising: wherein the removable percussion attachment provides percussion at the fixed or adjusted speeds 1200 rpm or 20 Hz, 1800 rpm or 30 Hz, 2400 rpm or 40 Hz, 3300 rpm or 55 Hz, 3900 rpm or 65 Hz; wherein the removable percussion attachment also provides percussion at the fixed or adjusted speeds of 900 rpm or 15 Hz, 4500 rpm or 75 Hz, 5100 rpm or 85 Hz, 5700 rpm or 95 Hz, and 6000 rpm or 100 Hz.

The method further comprising: wherein back and forth percussion of the percussion attachment is realized by a pushing rod; wherein a bushing supportively directs and protects the pushing rod; wherein the pushing rod is connected to a motor through a connecting rod and an eccentric wheel; wherein an Integrated Circuit board for motor control will convert the power of a battery to the motor; wherein the user feels the back and forth percussion on the user's skin from the device.

The method further comprising: wherein the removable percussion attachment is made of plastic, foam or metal.

The method further comprising: wherein the removable percussion attachment is made of any combination of plastic, foam and metal.

The method further comprising: wherein the device contains a removable battery on the bottom of the device; wherein the removable heating/cooling attachment provides cooling at the fixed or adjusted degrees of 6 degrees Celsius, 5 degrees Celsius, 4 degrees Celsius, 3 degrees Celsius, and 2 degrees Celsius; wherein the removable heating/cooling attachment also provides cooling through the clothing of the user at the fixed or adjusted temperatures of 1 degree Celsius, and 0 degrees Celsius; wherein the removable heating/cooling attachment provides heating at the fixed or adjusted degrees of 40 degrees Celsius, 41 degrees Celsius, 42 degrees Celsius, 43 degrees Celsius, and 44 degrees Celsius; wherein the removable heating/cooling attachment also provides heating through the clothing of the user at the fixed or adjusted temperatures of 45 degrees Celsius through 75 degrees Celsius at 1 degree increments; wherein the removable percussion attachment provides percussion at the fixed or adjusted speeds 1200 rpm or 20 Hz, 1800 rpm or 30 Hz, 2400 rpm or 40 Hz, 3300 rpm or 55 Hz, 3900 rpm or 65 Hz; wherein the removable percussion attachment also provides percussion at the fixed or adjusted speeds of 900 rpm or 15 Hz, 4500 rpm or 75 Hz, 5100 rpm or 85 Hz, 5700 rpm or 95 Hz, and 6000 rpm or 100 Hz; wherein the removable percussion attachment is made of plastic, foam, or metal, or any combination of plastic, foam and metal; wherein back and forth percussion of the percussion attachment is realized by a pushing rod; wherein a bushing supportively directs and protects the pushing rod; wherein the pushing rod is connected to a motor through a connecting rod and an eccentric wheel; wherein an Integrated Circuit board for motor control will convert the power of a battery to the motor; wherein the user feels the back and forth percussion on the user's skin from the device. A physical therapy device to provide physical therapy in the form of heating, cooling and/or percussion, comprising: a device that contains a battery, a motor, a knob for adjustment of speed or intensity, a button for angle adjustment of the front of the therapy device, and a switch to turn the physical therapy device on or off or put the physical therapy device in heating mode or put the physical therapy device in cooling mode or put the physical therapy device in percussion mode; wherein the physical therapy device contains a motor and a pushing rod that supply the movement that results in percussion of a removable heating/cooling attachment and a removable percussion attachment; wherein the front of the physical therapy device connects to the removable heating/cooling attachment that contains an electronic component to control heating or cooling and a cooling fan; wherein the removable heating/cooling attachment can be used for heating or cooling; wherein a housing shell for the heating/cooling attachment is made of plastic, foam, or metal, or any combination of plastic, foam and metal; wherein the front part of the heating/cooling attachment is made of metal that has the capability to be in contact with human skin in order to provide either heating or cooling at fixed or adjusted degrees that are optimal for physical therapy and/or blood circulation; wherein the removable heating/cooling attachment can be replaced by the removable percussion attachment that is used for percussion; wherein the removable percussion attachment can be placed on the skin of a user in order to provide percussion massage therapy at fixed or adjusted speeds that are optimal for physical therapy; wherein the physical therapy device contains a removable battery on the bottom of the physical therapy device; wherein the device contains a knob for adjustment of speed or intensity, and a button for angle adjustment of the front of the device; wherein the removable heating/cooling attachment provides cooling at the fixed or adjusted degrees of 6 degrees Celsius, 5 degrees Celsius, 4 degrees Celsius, 3 degrees Celsius, and 2 degrees Celsius; wherein the removable heating/cooling attachment also provides cooling through the clothing of the user at the fixed or adjusted temperatures of 1 degree Celsius, and 0 degrees Celsius; wherein the removable heating/cooling attachment provides heating at the fixed or adjusted degrees of 40 degrees Celsius, 41 degrees Celsius, 42 degrees Celsius, 43 degrees Celsius, and 44 degrees Celsius; wherein the removable heating/cooling attachment also provides heating through the clothing of the user at the fixed or adjusted temperatures of 45 degrees Celsius through 75 degrees Celsius at 1 degree increments; wherein the removable percussion attachment provides percussion at the fixed or adjusted speeds of 1200 rpm or 20 Hz, 1800 rpm or 30 Hz, 2400 rpm or 40 Hz, 3300 rpm or 55 Hz, 3900 rpm or 65 Hz; wherein the removable percussion attachment also provides percussion at the fixed or adjusted speeds of 900 rpm or 15 Hz, 4500 rpm or 75 Hz, 5100 rpm or 85 Hz, 5700 rpm or 95 Hz, and 6000 rpm or 100 Hz; wherein the removable percussion attachment is made of plastic, foam, metal, or any combination of plastic, foam and metal; wherein back and forth percussion of the percussion attachment is realized by a pushing rod; wherein a bushing supportively directs and protects the pushing rod; wherein the pushing rod is connected to a motor through a connecting rod and an eccentric wheel; wherein an Integrated Circuit board for motor control will convert the power of a battery to the motor; wherein the user feels the back and forth percussion on the user's skin from the device.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

It should also be noted that at least some of the operations for the methods described herein may be implemented using software instructions stored on a computer useable storage medium for execution by a computer. Embodiments of the invention can take the form of an entirely hardware embodiment, an entirely software embodiment, or an embodiment containing both hardware and software elements. In one embodiment, the invention is implemented in software, which includes but is not limited to firmware, resident software, microcode, etc.

Furthermore, embodiments of the invention can take the form of a computer program product accessible from a computer-usable or computer-readable storage medium providing program code for use by or in connection with a computer or any instruction execution system. For the purposes of this description, a computer-usable or computer readable storage medium can be any apparatus that can store the program for use by or in connection with the instruction execution system, apparatus, or device.

The computer-useable or computer-readable storage medium can be an electronic, magnetic, optical, electromagnetic, infrared, or semiconductor system (or apparatus or device), or a propagation medium. Examples of a computer-readable storage medium include a semiconductor or solid state memory, magnetic tape, a removable computer diskette, a random access memory (RAM), a read-only memory (ROM), a rigid magnetic disk, and an optical disk. Current examples of optical disks include a compact disk with read only memory (CD-ROM), a compact disk with read/write (CD-R/W), and a digital video disk (DVD).

An embodiment of a data processing system suitable for storing and/or executing program code includes at least one processor coupled directly or indirectly to memory elements through a system bus such as a data, address, and/or control bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers. Additionally, network adapters also may be coupled to the system to enable the data processing system to become coupled to other data processing systems or remote printers or storage devices through intervening private or public networks. Modems, cable modems, and Ethernet cards are just a few of the currently available types of network adapters.

Although specific embodiments of the invention have been described and illustrated, the invention is not to be limited to the specific forms or arrangements of parts so described and illustrated. The scope of the invention is to be defined by the claims appended hereto and their equivalents.

The present invention is described in the preceding on the basis of several preferred embodiments. Different aspects of different variants are considered to be described in combination with each other such that all combinations that upon reading by a skilled person in the field on the basis of this document can be regarded as being read within the concept of the invent ion. The preferred embodiments do not limit the extent of protection of this document. The requested rights are laid down in the appended claims.

We claim:

1. A portable percussion massager comprising:
a housing;
a motor positioned within the housing that is rotatably coupled to a connecting rod;
a pushing rod coupled to the connecting rod for creating a percussive massage effect; and
a temperature-controlled massage attachment electrically and removably coupled to the pushing rod at its end opposite attachment to the connecting rod, the temperature-controlled massage attachment includes an attachment housing, the attachment housing having a fan and a semiconductor positioned within the attachment housing, where the semiconductor, upon activation, cools the temperature-controlled massage attachment, where the fan is activated only when the semiconductor is cooling the temperature-controlled massage attachment, and where the attachment housing further includes a skin contact medium for covering the semiconductor to prevent direct contact by a user with the semiconductor.

2. The portable percussion massager of claim 1 where the temperature-controlled massage attachment upon activation of the semiconductor, cools the temperature-controlled massage attachment to at least one predetermined temperature.

3. The portable percussion massager of claim 1 where the temperature-controlled massage attachment, upon activation of the semiconductor, cools the temperature-controlled massage attachment to at least two predetermined temperatures.

4. The portable percussion massager of claim 1 where the skin contact medium is a metal contact plate.

5. The portable percussion massager of claim 1 where the massage attachment includes first electrical contacts and where the housing includes a jack having second electrical contacts for pairing with the first electrical contacts on the massage attachment to supply power to the semiconductor within the temperature-controlled massage attachment.

6. The portable percussion massager of claim 1 where the temperature-controlled massage attachment and motor are electrically connected to the same power source.

7. A percussion massager having a percussion massage attachment, the percussion massager comprising:
- a percussion massager housing;
- a percussion massage attachment that is electrically and removably coupled to the percussion massager housing, where the percussion massage attachment includes:
- an attachment housing having a lower and an upper portion;
- a contact plate positioned on the upper portion of the attachment housing;
- a semiconductor plate positioned within the attachment housing below the contact plate for heating and cooling the contact plate;
- an indication display including at least one LED positioned on a mounting surface, where the indication display illuminates light in a first color when the semiconductor plate is heating the contact plate and a second color when the semiconductor plate is cooling the contact plate; and
- a fan positioned within the attachment housing, where the fan is activated only when the semiconductor plate is cooling the contact plate.

8. The percussion massager having a percussion massage attachment of claim 7 where the indication display is located on the percussion massager housing.

9. The percussion massager having a percussion massage attachment of claim 7, where the at least one LED is a multi-colored LED, where the at least one LED illuminates in a first state when the semiconductor plate is heating the attachment and second state when the semiconductor plate is cooling the attachment.

10. The percussion massager having a percussion massage attachment of claim 7 where the contact plate is either heated or cooled by the semiconductor plate and where the at least one LED illuminates a first color when contact plate is heated and a second color when the contact plate is cooled.

11. The percussion massager having a percussion massage attachment of claim 10, where the first color is a shade of red and the second color is a shade of blue.

12. The percussion massager having a percussion massage attachment of claim 7, where the at least one LED is a first LED that illuminates in a first color when the semiconductor plate is heating the attachment and a second LED that illuminates in a second color when the semiconductor plate is cooling the attachment.

13. The percussion massager having a percussion massage attachment of claim 12, where the first color is a shade of red and the second color is a shade of blue.

14. A percussion massager comprising:
- a percussion massager housing;
- a motor within the percussion massager housing driving a pushing rod having a first electrical contact;
- a massage attachment, where the massage attachment is temperature controlled and includes an attachment housing having a lower and upper shell and a second electrical contact on the lower shell of the attachment housing, where the second electrical contact removably and electrically couples to the first electrical contact of the pushing rod of the percussion massager;
- a semiconductor positioned within the attachment housing, the semiconductor in communication with the first electrical contact; and
- a skin contact medium positioned on the upper portion of the massage attachment, where the semiconductor provides cooling to the skin contact medium; and
- a fan positioned within the attachment housing, where the fan is activated only when the semiconductor provides cooling to the skin contact medium.

15. The percussion massager of claim 14, where the semiconductor both cools and heats the skin contact medium.

16. The percussion massager of claim 14, where the massage attachment further includes a temperature sensor.

17. The percussion massager of claim 14, where the massage attachment further includes a heat sink within the attachment housing.

18. The percussion massager of claim 14, where the fan is in communication with the first electrical contact.

19. The percussion massager of claim 14, where the attachment housing includes vents for dissipating heat.

20. A portable percussion massager comprising:
- a housing;
- a motor within the housing driving a pushing rod;
- at least one temperature-controlled massage attachment removably coupled to the pushing rod, where the temperature-controlled massage attachment includes first electric contacts and where the housing includes a jack for coupling with the first electrical contacts on the temperature-controlled massage attachment, the temperature-controlled massage attachment including a semiconductor to either or both heat and cool the massage attachment; and
- a fan positioned within the attachment housing, where the fan is activated only when the semiconductor is cooling the massage attachment.

21. The portable percussion massager of claim 20 where the first electric contacts are electrical pins.

22. The portable percussion massager of claim 20 where the massage attachment includes a plurality of vent openings for dissipating heat.

23. The portable percussion massager of claim 20 where the housing further includes a power source.

24. The portable percussion massager of claim 23 where the massage attachment and motor are electrically connected to the same power source.

* * * * *